United States Patent
Franzèn et al.

(10) Patent No.: US 10,054,596 B2
(45) Date of Patent: Aug. 21, 2018

(54) PLATELET BIOMARKERS IN CANCER DIAGNOSIS

(71) Applicant: NEOPROTEOMICS AB, Stockholm (SE)

(72) Inventors: Bo Franzèn, Nacka (SE); Gert Auer, Solna (SE); Susanne Becker, Drottningholm (SE); Marta Lomnytska, Upplands Väsby (SE); Timo Gemoll, Grossenbrode (DE); Jens Habermann, Celle (DE)

(73) Assignee: NEOPROTEOMICS AB, Stockholm (SE)

( * ) Notice: Subject to any disclaimer, the term of this patent is extended or adjusted under 35 U.S.C. 154(b) by 61 days.

(21) Appl. No.: 14/762,394

(22) PCT Filed: Jan. 22, 2014

(86) PCT No.: PCT/SE2014/050075
§ 371 (c)(1),
(2) Date: Jul. 21, 2015

(87) PCT Pub. No.: WO2014/116170
PCT Pub. Date: Jul. 31, 2014

(65) Prior Publication Data
US 2015/0369817 A1    Dec. 24, 2015

Related U.S. Application Data

(60) Provisional application No. 61/755,294, filed on Jan. 22, 2013.

(30) Foreign Application Priority Data

Jan. 22, 2013   (SE) ..................... 1350063

(51) Int. Cl.
G01N 33/53   (2006.01)
G01N 33/68   (2006.01)
G01N 33/574  (2006.01)

(52) U.S. Cl.
CPC ... *G01N 33/6848* (2013.01); *G01N 33/57438* (2013.01); *G01N 33/57446* (2013.01); *G01N 33/57488* (2013.01); *G01N 33/57492* (2013.01); *G01N 33/57496* (2013.01); *G01N 33/6893* (2013.01); *G01N 2496/00* (2013.01); *G01N 2560/00* (2013.01); *G01N 2800/50* (2013.01); *G01N 2800/7028* (2013.01)

(58) Field of Classification Search
None
See application file for complete search history.

(56) References Cited

U.S. PATENT DOCUMENTS

| | | |
|---|---|---|
| 8,173,433 B2 | 5/2012 | Folkman et al. |
| 2009/0042229 A1 | 2/2009 | Folkman et al. |
| 2009/0131356 A1 | 5/2009 | Bader et al. |
| 2011/0003298 A1 | 1/2011 | Liew |
| 2012/0230089 A1 | 9/2012 | Yamada et al. |
| 2013/0178386 A1 | 7/2013 | Folkman et al. |
| 2014/0162888 A1 | 6/2014 | Kuslich et al. |

FOREIGN PATENT DOCUMENTS

| | | |
|---|---|---|
| AT | 500719 A1 | 3/2011 |
| JP | 2007535324 A | 12/2007 |
| JP | 2008508538 A | 3/2008 |
| JP | 2010504102 A | 2/2010 |
| WO | 2005/103281 A2 | 11/2005 |
| WO | 2006/022895 A2 | 3/2006 |
| WO | 2008/036765 A2 | 3/2008 |
| WO | 2011/033873 A1 | 3/2011 |
| WO | 2011/127219 A1 | 10/2011 |
| WO | 2012/054732 A2 | 4/2012 |
| WO | 2012/087983 A1 | 6/2012 |

OTHER PUBLICATIONS

Gabrovska et al (Mol Biol Rep, 2012, 39: 3879-3892).*
Endo et al (International Journal of Oncology, 2009, 35: 499-509).*
Hillmann et al (Journal of Thrombosis and Haemostasis, 2006, 4: 349-356).*
Piersma et al (The Journal of Proteomics, 2009, 72: 91-109).*
Official Action from corresponding European Application No. 14743417.9, dated Oct. 10, 2016.
Choi et al., Expression of B-tubulin Isotypes in Urothelial Carcinoma of the Bladder, World J. Urol, p. 1-6 (Published online Nov. 27, 2012).
Huang et al., Discovery of Serum Biomarkers Implicated in the Onset and Progression of Serous Ovarian Cancer in a Rat Model Using iTRAQ Technique, European Journal of Obstetrics & Gynecology and Reproductive Biology, 165:96-103 (2012).
Hellman et al., Differential Tissue-Specific Protein Markers of Vaginal Carcinoma, British Journal of Cancer, 100:1303-1314 (2009).
Erpenbeck et al., Deadly Allies: The Fatal Interplay Between Platelets and Metastasizing Cancer Cells, Blood, 115 (17):3427-3436 (Prepublished online Mar. 1, 2010).
English Translation of Official Action dated Dec. 1, 2017 from corresponding Japanese Application No. 2015-553679.

(Continued)

*Primary Examiner* — Sean E Aeder
(74) *Attorney, Agent, or Firm* — Porter Wright Morris & Arthur LLP

(57) ABSTRACT

The present embodiments relate generally to the field of cancer diagnostics. More specifically the embodiments relate to platelet derived biomarkers used for diagnosis of cancer or cancer progression, as well as prognosis and improved treatment.

5 Claims, 11 Drawing Sheets

(56) References Cited

OTHER PUBLICATIONS

Gagne et al, Comparative proteome analysis of human epithelial ovarian cancer, Proteome Science, published on line Sep. 24, 2007, pp. 1-15.

* cited by examiner

PLATELET BIOMARKERS IN CANCER DIAGNOSIS

TECHNICAL FIELD

The present embodiments generally relate to the field of cancer diagnosis. More specifically the embodiments relate to platelet biomarkers used in cancer diagnosis.

BACKGROUND

Cancer, known medically as a malignant neoplasm, is a broad group of diseases involving unregulated cell growth. In cancer, cells divide and grow uncontrollably, forming malignant tumors, and invading nearby parts of the body. The cancer may also spread to more distant parts of the body through the lymphatic system or bloodstream. Not all tumors are cancerous; benign tumors do not invade neighboring tissues and do not spread throughout the body. There are over 200 different known cancers that affect humans.

Cancer can be detected in a number of ways, including the presence of certain signs and symptoms, screening tests, or medical imaging. Once a possible cancer is detected it is usually diagnosed by microscopic examination of a tissue sample from a tissue biopsy. Detecting and diagnosing cancers early on is essential when it comes to treatment outcome and survival, especially when it comes to highly malignant tumors.

Carcinoma, also often denoted epithelial cancer in the art, the most common type of malignant neoplasia (cancer) occurring in humans, is a tumor tissue derived from putative epithelial cells whose genome has become altered or damaged to such an extent that the cells become transformed, and begin to exhibit abnormal malignant properties. Carcinomas can be diagnosed through biopsy, including fine-needle aspiration (FNA), core needle biopsy, or surgical biopsy. Microscopic examination by a pathologist is necessary to identify cellular or tissue architectural characteristics as well as tissue specific biomarker patterns.

Increasing evidence indicates that diagnostic biopsies of possible cancers may induce tumor cell dissemination and subsequently distant metastases. There is therefore an urgent need to substitute the hazardous tumor tissue sampling biopsy procedures by diagnostic methods not traumatizing the tumor tissue causing cancer spread, but still having the possibility to detect and diagnose cancer early on. A patient friendly, simple and risk-free detection and diagnosis of cancer and cancer status is therefore needed. Especially regarding the most highly malignant cancers, ovarian, pancreatic and colorectal, it is very desirable to be able to perform an early non-invasive diagnosis to save lives. Also, to be able to diagnose malignant prostate cancer with a non-invasive procedure would be very beneficial, since taking prostate biopsies are particularly problematic. All these cancers are typically classified carcinoma, i.e. cancers of epithelial cell origin.

Ovarian cancer is a cancerous growth arising from the ovary, wherein suspected cancer needs to be confirmed with surgery to inspect the abdominal cavity, biopsies and detection of cancer cells in the abdominal fluid. These procedures are both cumbersome and risky for the patient. Due to asymptomatic development, ovarian cancer is often diagnosed at an advanced stage, with a poor prognosis. An easily performed test that could confirm cancer and cancer status would therefore be very beneficial for the diagnosis of ovarian cancers.

Most ovarian cancers are classified as "epithelial" and arise from the epithelium of the ovary. Epithelial ovarian cancer (EOC) is the deadliest of all gynaecologic malignancies-EOC develops asymptomatically, and is in the majority of cases detected at an advanced stage. Due to its notorious capability for asymptomatic growth and spread in the abdominal cavity, curative treatment is then difficult to achieve. Tumour markers for EOC (e.g. CA-125) are in clinical use today. Due to the low specificity they are only used as supportive information together with ultrasound and physical examination, but offer limited sensitivity. Measuring the levels of CA-125 has bigger value during the monitoring during treatment of ovarian cancer. For example, in one study, CA-125 was used in the assessment of patients presenting with a pelvic mass. Elevated CA-125 levels had a sensitivity of 72% and specificity of 78% for ovarian cancer (positive predictive value of 72% and a negative predictive value of 78%). However, in another study, sensitivity for early-stage disease was only 40% (Skates S J, et al. Preoperative sensitivity and specificity for early-stage ovarian cancer when combining cancer antigen CA-125II, CA 15-3, CA 72-4, and macrophage colony-stimulating factor using mixtures of multivariate normal distributions.

Preoperative biopsy and other rupturing injury of suspect cancer lesions are strongly contraindicated due to the high risk of spread of EOC. Instead, expert gynaecologic ultrasound is the method of choice in assessment of adnexal masses. However, in many cases even an experienced medical examiner cannot provide conclusive answers.

To reach significant progress, there is an urgent need to improve the means for early detection of EOC, and following detection, the means to discriminate benign and malignant lesions, as a prerequisite for a differentiated optimized treatment.

Trombocytosis is a common observation in patients with progressing cancer, and has also been specifically associated with worse prognosis and early relapse in patients operated for non-advanced EOC. There is also increasing, intriguing evidence that platelets, beyond their participation in hemostasis, can influence angiogenic and immunological processes and thereby decisively contribute to tumor development.

Proteomic analyses of platelets have shown that angiogenic factors can be sequestered by platelets, and then specifically released and delivered to sites of activated endothelium within early tumours. A so-called "metastatic/malignant platelet phenotype" could be observed in patients with different newly diagnosed metastatic diseases.

Prostate cancer is a type of cancer that develops in epithelial prostate tissue. Today prostate cancer is diagnosed using prostate-specific antigen (PSA). This is merely an indicative method and is not specific for malignant cancer. Due to this fact there is always multiple biopsies taken for confirmatory diagnosis. Taking biopsies is unpleasant for the patient and reported to be associated with serious side effects. Several patients have to visit the emergency room even the same day for sepsis as an effect from the biopsy. Impotency is also a side effect that is rather frequent. The most dangerous effect longer term is that cancer cells actually leak out from the prostate gland during the biopsy. These cancer cells can then spread and potentially cause metastasis. In prostate cancer about 70% are of low malignancy and not in need of immediate or aggressive treatment. Therefore, tests that can indicate cancer, and also can distinguish the high malignancies from the low malignancies are highly sought after. It is within the scope of the invention to provide a test that can fulfil these criteria. The global incidence of prostate cancer is about 900,000 per year. If all of these were tested using the test of the invention, about 600,000 men per year would not have to be tested using unpleasant and potentially harmful biopsies. Thus, a way to diagnose prostate cancer without the need of a biopsy is desirable.

Pancreatic cancer is a malignant neoplasm originating from transformed cells arising in tissues forming the pancreas. The most common type of pancreatic cancer, accounting for 95% of these tumors, is adenocarcinoma (tumors exhibiting glandular architecture on light microscopy) arising within the exocrine component of the pancreas. A minority arises from islet cells, and are classified as neuroendocrine tumors. The signs and symptoms that eventually lead to the diagnosis depend on the location, the size, and the tissue type of the tumor, and may include abdominal pain, lower back pain, and jaundice (if the tumor compresses the bile duct), unexplained weight loss, and digestive problems. Pancreatic cancer is the fourth most common cause of cancer-related deaths in the United States and the eighth worldwide. Pancreatic cancer has an extremely poor prognosis: for all stages combined, the 1- and 5-year relative survival rates are 25% and 6%, respectively; for local disease the 5-year survival is approximately 15% while the median survival for locally advanced and for metastatic disease, which collectively represent over 80% of individuals, is about 10 and 6 months, respectively. Individuals vary, however—some are only diagnosed when they are already terminally ill and therefore only have a few days or weeks. Others have slower progression and may live a couple of years even if surgery is not possible. Men are 30% more likely to get pancreatic cancer than are women.

Pancreatic cancer is one of the most lethal malignancies worldwide and thus demonstrates an urgent demand for improved screening tools for early detection. Diagnosis of pancreatic cancer at early stages is crucial because successful surgery at early tumor stages is the only curative therapy today. Only 10-30% of pancreatic tumor patients are operated with curative intend, and of theses, only half actually undergo RO resection. The expected 5-year survival rate of RO resected patients with additional adjuvant chemotherapy is about 4-26%.

A diagnostic test for early detection is here highly sought after. The challenge is to find if there is a time-window between the start of the cancer in the body and before it is too late for starting treatment. If this window is big enough a diagnostic method is extremely valuable. Due to the high malignancy and aggression of the disease, it is highly desirable to find a way to diagnose pancreatic cancer early, preferably without the hazardous procedure of taking a biopsy.

Colorectal cancer, also known as colon cancer, rectal cancer, or bowel cancer, is a cancer from uncontrolled cell growth in the colon or rectum (parts of the large intestine), or in the appendix. Genetic analysis shows that essentially colon and rectal tumours are genetically the same cancer. Symptoms of colorectal cancer typically include rectal bleeding and anemia which are sometimes associated with weight loss and changes in bowel habits. Most colorectal cancer occurs due to lifestyle and increasing age with only a minority of cases associated with underlying genetic disorders. It typically starts in the lining of the bowel and if left untreated, can grow into the muscle layers underneath, and then through the bowel wall. Screening is effective at decreasing the chance of dying from colorectal cancer and is recommended starting at the age of 50 and continuing until a person is 75 years old. Localized bowel cancer is usually diagnosed through sigmoidoscopy or colonoscopy. Cancers that are confined within the wall of the colon are often curable with surgery while cancer that has spread widely around the body is usually not curable and management then focuses on extending the person's life via chemotherapy and improving quality of life. Colorectal cancer is the third most commonly diagnosed cancer in the world, but it is more common in developed countries. Around 60% of cases were diagnosed in the developed world. It is estimated that worldwide, in 2008, 1.23 million new cases of colorectal cancer were clinically diagnosed, and that it killed 608,000 people.

Colon cancer ranks among the most frequent malignancies and is the fourth leading cause of cancer-related death worldwide. Detection of colon cancer at early stages is critical for curative treatment interventions: although the 5-year disease-free survival for International Union Against Cancer (UICC) stage I tumors exceeds 90%, this rate is reduced to 63% in UICC III and <5% in UICC IV carcinomas. Yet, despite the implementation of current screening programs about 50% of these malignancies are detected at advanced tumor stages. Colorectal cancer is today diagnosed using imaging techniques combined with colonoscopy. There are biomarker tests are available in the market, but none of these biomarker tests are good enough for use in clinical diagnostics. Thus, it would also be highly desirable to find a way to diagnose pancreatic cancer early, preferably without the riskful procedure of taking a biopsy.

There is therefore a general need for a technology enabling early detection of cancer since it would allow for a more effective treatment of patients and hence a higher survival rate. Further, it would also be beneficial if the technology can be used to determine the progression of the cancer, i.e. if it is in an early or advanced stage since early, often local, or advanced, often disseminated malignancies, require different treatment alternatives, and are characterized by a different prognosis.

U.S. Pat. No. 8,173,433 describes an early detection of clinical conditions having associated changes in systemic angiogenic activity, particularly cancers, inflammatory conditions, infections, and events associated with pregnancy and abortion.

SUMMARY

It is a general objective to provide an improved technology that can be used within cancer diagnosis.

It is a particular objective to provide an improved technology that can be instead of biopsy for cancer diagnosis.

These and other objectives are met by embodiments disclosed herein.

An aspect of the embodiments relates to a method of determining whether a subject is suffering from a benign lesion or from a carcinoma lesion. The method comprises measuring at least two platelet-derived biomarkers in a biological sample from the subject. The at least two platelet-derived biomarkers are selected from a group consisting of α-actinin 1 (ACTN1), α-actinin 4 (ACTN4), crk-like protein (CRKL), endoplasmic reticulum protein 29 (ERP29), (FERM), fibrinogen gamma chain (FGG), filamin A (FLNA), gelsolin (GELS), mitochondrial stress-70 protein (GRP75), HP protein, heat shock protein 70 kDa (HSP70), heat shock protein 71 kDa (HSP71), of integrin alpha-2b (ITGA2B), integrin beta-3 (ITB3), ribonuclease inhibitor (RINI), proto-oncogene tyrosine-protein kinase Src (SRC), tubulin (TBB), tubulin alpha-4A chain (TBA4A), 3-mercaptopyruvate sulfurtransferase (THTM), talin-1 (TLN1), tubulin beta-1 chain (TUBB1), vinculin (VCL) and WD repeat containing protein 1 (WDR1). The method also comprises determining whether the subject is suffering from the benign lesion or from the carcinoma lesion based on the measurement.

Another aspect of the embodiments relates to a method of predicting existence of a benign and/or carcinoma lesion in a subject. The method comprises measuring at least two platelet-derived biomarkers in a biological sample from the subject. The at least two platelet-derived biomarkers are selected from a group consisting of diadenosine tetraphosphate (AP4A), F-actin capping protein subunit alpha-1 (CAZA1), cytosol non-specific dipeptidase (CNDP2), glycoprotein IX (GPIX), leukocyte elastase inhibitor (ILEU), cAMP-dependent protein kinase subunit RII-beta (KAP3), prohibitin (PHB), endophilin-B1 (SHLB1), serpin B6 (SPB6) and tropomyosin alpha-1 (TMP1). The method also comprises predicting existence of the benign and/or carcinoma lesion in the subject based on the measurement.

A further aspect of the embodiments relates to a method of predicting existence of colorectal or pancreas cancer in a subject. The method comprises measuring at least two platelet-derived biomarkers in a biological sample from the subject. The at least two platelet derived biomarkers are selected from a group consisting of beta-actin (ACTB), ACTN1, caspase 3 (CASP3), cofilin 1 (CLF1), clusterin (CLU), farnesyl pyrophosphate synthase (FPPS), GELS, glutathione S-transferase omega-1 (GSTO1), heat shock protein HSP 90-beta (HSP90AB1), haloacid dehalogenase-like hydrolase domain-containing protein 2 (HDHD2), ITGA2B, ITB3, integrin alpha-6 (ITGA6), malectin (MLEC), prohibitin (PHB), RINI, alpha-synuclein (SNCA), serpin B6 (SPB6), TBA4A, TLN1, tumor susceptibility gene 101 protein (TSG), TBB1, VCL and WDR1. The method also comprises predicting existence of the colorectal or pancreas cancer in the subject based on said measurement.

Yet another aspect of the embodiments relates to a method of predicting existence of carcinoma in a subject. The method comprises measuring at least two platelet-derived biomarkers in a biological sample from the subject. The at least two platelet derived biomarkers are selected from a group consisting of ACTN1, GELS, ITGA2B, ITB3, PHB, RINI, SPB6, TBA4A, TLN1, TBB1, VCL and WDR1. The method also comprises predicting existence of the carcinoma in the subject based on the measurement.

A further aspect of the embodiments relates to a method of selecting a cancer treatment regimen for a subject. The method comprises determining whether the subject is suffering from a benign lesion or from a carcinoma lesion according to above; predicting existence of a benign and/or carcinoma lesion in the subject according to above; predicting existence of colorectal or pancreas cancer in the subject according to above; or predicting existence of carcinoma in the subject according to above. The method also comprises selecting treatment regimen for the subject based on whether the subject is suffering from the benign lesion or from the carcinoma lesion; based on the predicted existence of the benign and/or carcinoma lesion in the subject; based on the predicted existence of the colorectal or pancreas cancer in the subject; or based on the predicted existence of the carcinoma in the subject.

The embodiments allow for a patient friendly cancer prediction based on a biological sample. This patient friendly and easy way of obtaining information about the cancer status by using, for instance, a blood sample is a great tool for cancer diagnostics without the need for taking biopsies. The present embodiments will provide a safe and accurate diagnostic tool potentially enabling personalized cancer treatment. Thus, instead of the hazardous procedure of taking a biopsy, the non-invasive procedure of the embodiments could be used, enabling, for instance, discrimination between benign lesions and early stage carcinoma lesions, thus performing diagnosis of malignant cancer at an early stage.

Embodiments as disclosed herein can be used as an objective tool for non-invasive cancer diagnosis, including screening, clinical diagnosis of suspected cancers and hereditary indications, for follow-up of treatment of the cancer and for monitoring of potential recurrence. The embodiments can also potentially be used as a Companion Diagnostic together with various treatment regimes. The tool could be used for detection of lesions that might be malignant, such as discriminating between healthy subjects and subject with benign or malignant lesions, for prediction, determination or evaluation of cancer status and/or prediction, determination or evaluation of cancer progression status.

The embodiments allow for a patient friendly non-invasive cancer status prediction based on a biological sample. This patient friendly and easy way of obtaining information about the cancer status by using, for instance, a blood sample is a great tool for cancer diagnostics without the need for taking biopsies. The present embodiments will provide a safe and accurate diagnostic tool potentially enabling personalized cancer treatment.

BRIEF DESCRIPTION OF THE DRAWINGS

The invention, together with further objects and advantages thereof, may best be understood by making reference to the following description taken together with the accompanying drawings, in which.

Software module: Data is taken in and analyzed by a specific algorithm. The data is then compared to a prediction model that is built from patient data during the development of the assay. The prediction model provides for each new sample a value between 0 and 1, where values >0.5 indicate cancer and values <0.5 indicate benign lesions. This procedure will be used to continuously build a local prediction database using standardized procedures and in addition, results may be compared with the corresponding databases from other certified analysis laboratories.

Figure 8:
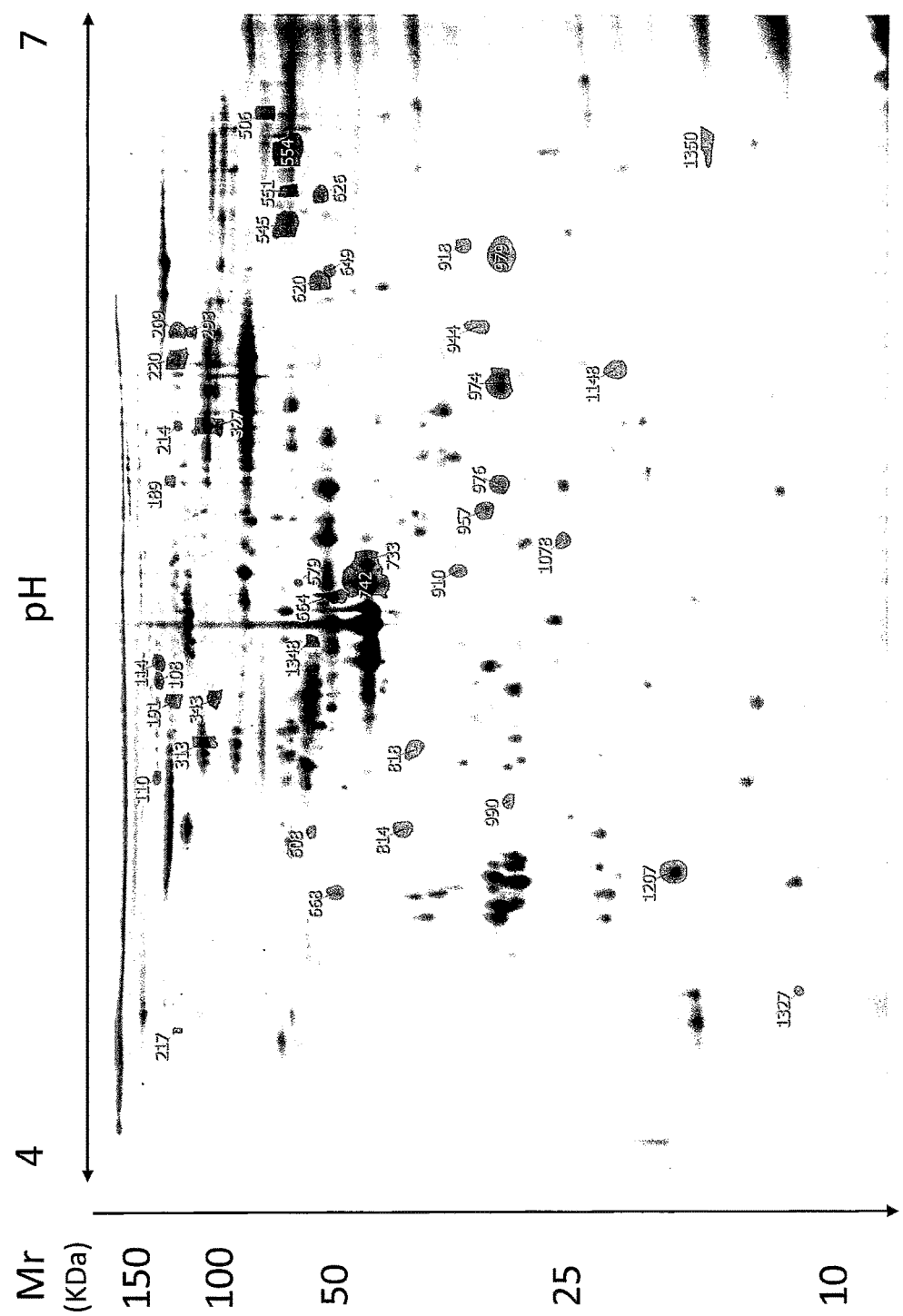

FIG. 8 shows a representative 2D gel image where differentially expressed proteins are marked (numbers) from study 3 and 4. These proteins were identified in platelets from patients suffering from colorectal cancer and pancreatic cancer. All identities are described in table 7 and 8.

Figure 9:
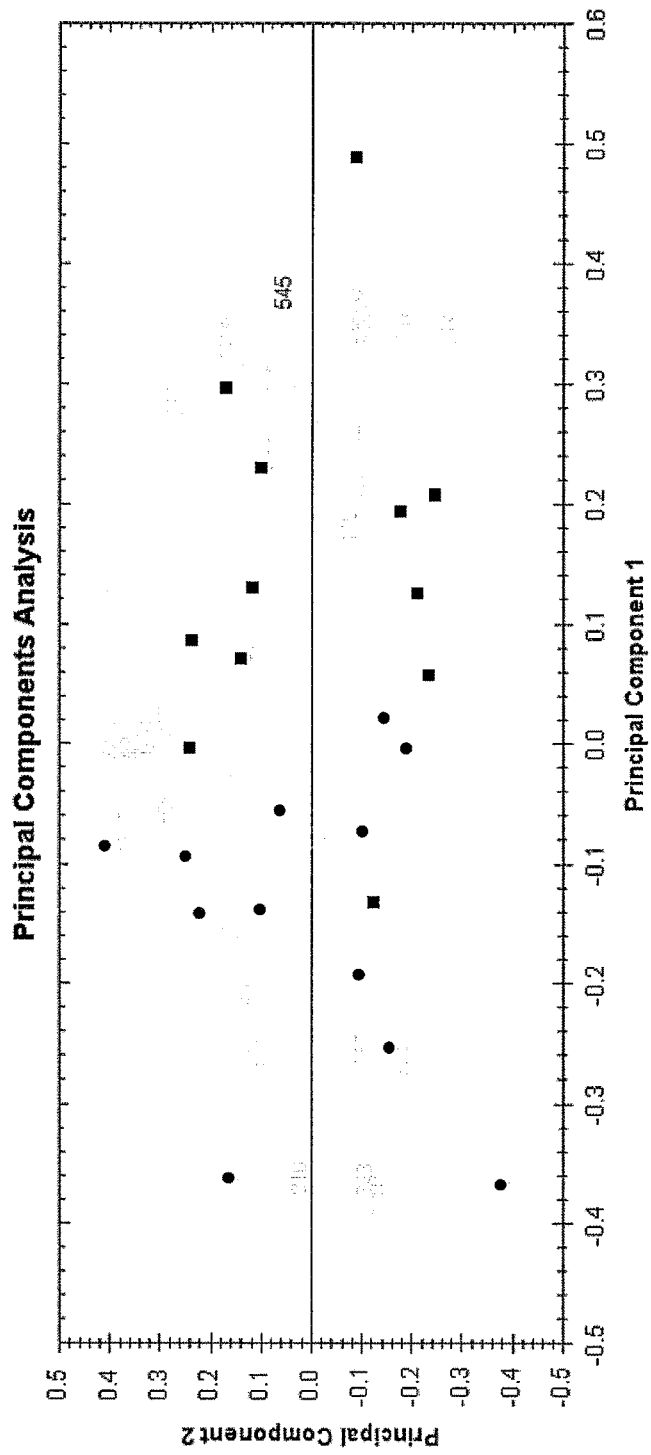

FIG. 9 shows a PCA (principal component analysis) from study 3 of the separation between samples (objects) representing healthy controls (squares) and colorectal cancers (dots) based on the differential expression levels of the identified biomarkers described in table 7. The numbers represent individual protein spots (variables) as loadings in the analysis.

Figure 10:
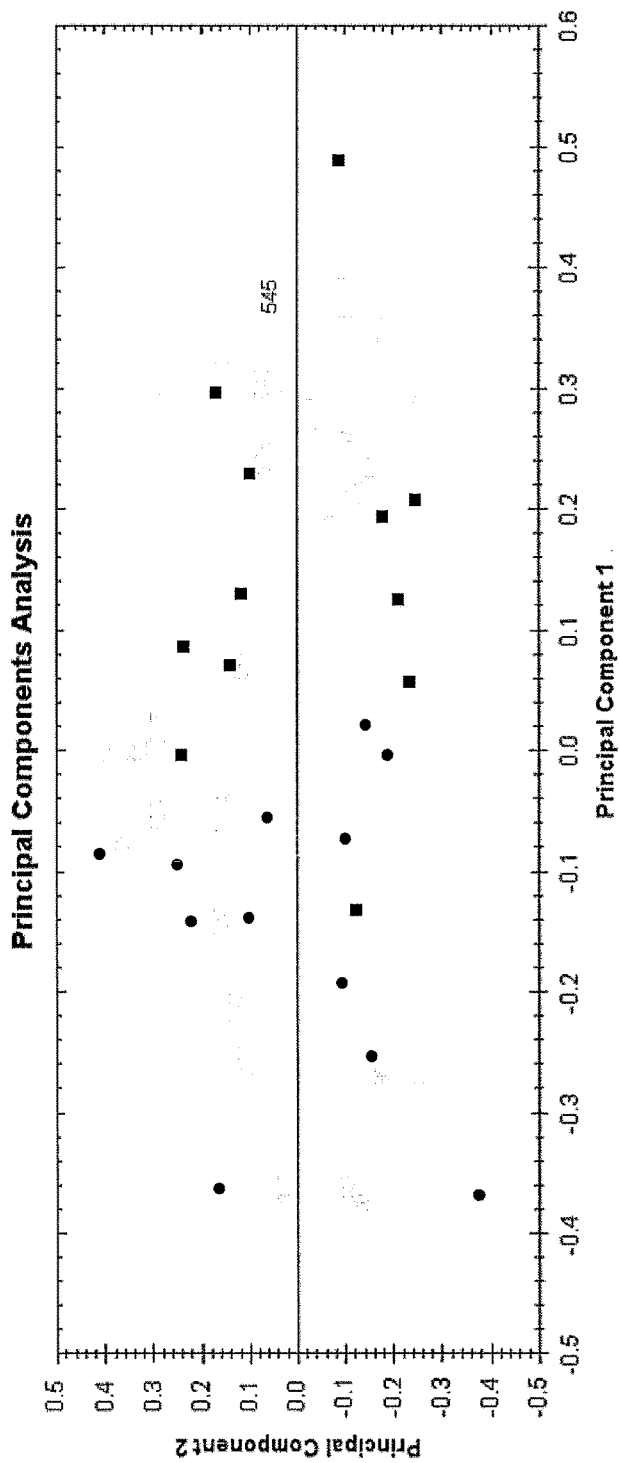

FIG. 10 shows a PCA (principal component analysis) from study 4 of the separation between samples representing healthy controls (squares) and pancreatic cancers (dots) based on the differential expression levels of the identified biomarkers described in table 8. The numbers represent individual protein spots (variables) as loadings in the analysis.

Figure 11:
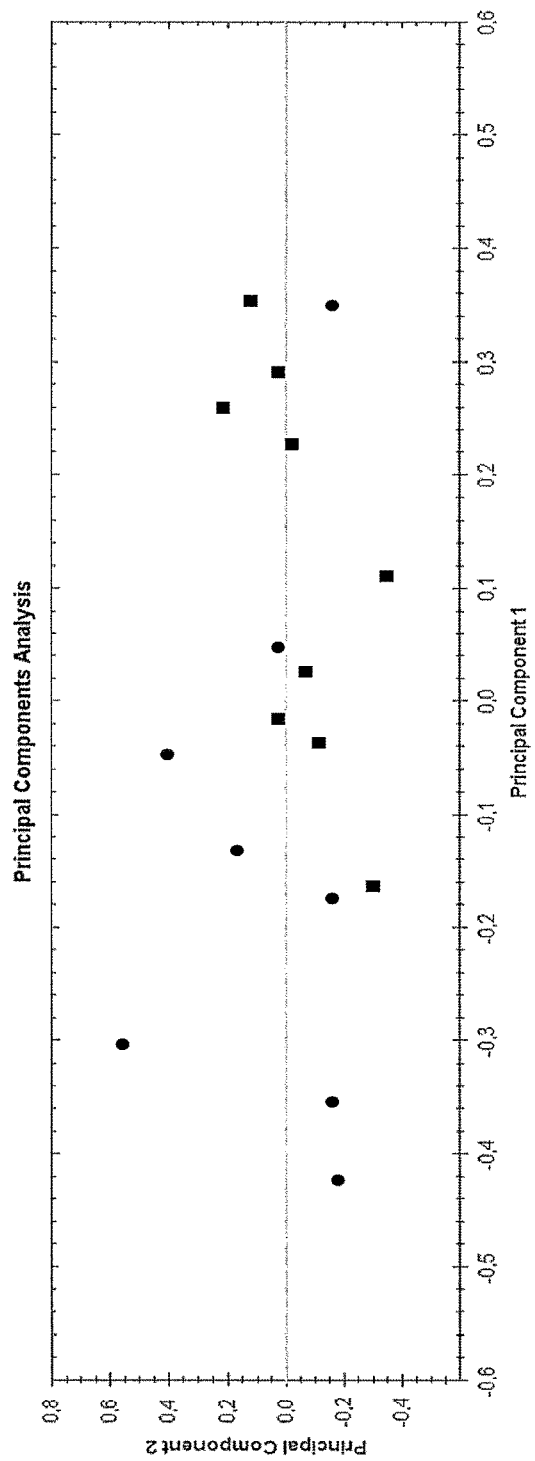

FIG. 11 shows a PCA (principal component analysis) of the separation between samples (objects) representing healthy controls (squares) and prostate cancers (dots) based on the differential expression levels of candidate biomarkers.

DETAILED DESCRIPTION

The present embodiments generally relate to the field of cancer diagnosis. More specifically the embodiments relate to platelet biomarkers used in epithelial cancer prediction and diagnosis.

The present embodiments, hence, use a combination of selected platelet-derived proteins as biomarkers. It has been found that the platelet-derived proteins of the embodiments can be used in an efficient, reliable and safe way in cancer diagnosis of a subject, preferably a mammalian subject and more preferably a human subject.

It is this within the scope of the embodiments to allow for simple, patient friendly and risk free detection/diagnosis of cancer and cancer status, particularly for carcinomas or "epithelial" cancers, possible already at an early stage of the disease. Early detection of cancer is desirable since it allows for a more effective treatment of patients and hence a higher survival rate. Further, it is also advantageous to be able to determine the progression of the cancer, if it is in an early or advanced stage since early, often local, or advanced, often disseminated malignancies, require different treatment alternatives, and are characterized by a different prognosis.

In clear contrast to the embodiments, U.S. Pat. No. 8,173,433 mentioned in the background section discloses that angiogenic platelet proteins may be used as biomarkers for detection of cancer. The angiogenic proteins disclosed therein are involved in the process through which new blood vessels form from pre-existing vessels. Such new blood vessels are generally important for tumor growths in order to provide sufficient nutrient and oxygen to the growing cancer cells. Angiogenesis is also important for metastasis, i.e. provides a route that can be used for metastasizing tumors to spread to other loci within the subject body.

The methods disclosed in U.S. Pat. No. 8,173,433 typically require at least two samples taken from the same subject at two different time points. The two samples are analyzed and the angiogenic protein pattern is compared to see changes from one time point to another in order to determine cancer status.

The present embodiments are based on new panels of platelet-derived proteins that may be used for cancer diagnostic. The proteins represented in these panels are, surprisingly and in clear contrast to U.S. Pat. No. 8,173,433, not limited to angiogenic proteins.

The platelet-derived biomarkers of the present embodiments can be used for various diagnostic purposes within the field of cancer diagnosis depending on the selected combination of the platelet-derived biomarkers. For instance, a selected panel of platelet-derived biomarkers can be used to classify a lesion in a subject as either being benign or being a malignant lesion, preferably a carcinoma or epithelial cancer lesion. Thus, the selected panel of platelet-derived biomarkers can be used to determine whether a subject is suffering from a benign lesion or from a carcinoma lesion.

Furthermore, another selected panel of the platelet-derived biomarkers of the embodiments can be used to classify a subject as either being healthy or suffering from a benign and/or malignant lesion, preferably suffering from a benign and/or carcinoma lesion. Hence, this selected panel of platelet-derived biomarkers can be used to predict the existence of a benign and/or carcinoma lesion in a subject.

A selected panel of the platelet-derived biomarkers of the embodiments can be used for general cancer diagnosis, i.e. determining whether a subject is suffering from cancer, in particular suffering from a carcinoma, such as suffering from colorectal or pancreas cancer. Thus, this selected panel of platelet-derived biomarkers can be used to predict the existence of colorectal or pancreas cancer in a subject. The platelet-derived biomarkers of the embodiments can also be used not only to predict existence of carcinoma in a subject but also for prediction of existence of early stage carcinoma.

Another selected panel of the platelet-derived biomarkers of the embodiments can be used in cancer diagnosis to classify a malignant lesion as being in an early stage. This panel of platelet-derived biomarkers could thereby be used to monitor cancer progression and possibly discriminate between early stage and late stage malignant lesions and in particular early or late stage carcinoma. Hence, the selected panel of platelet-derived biomarkers can be used to predict the existence of early stage carcinoma in a subject.

Some of the terms used herein are clarified here below in order to simplify understanding of the disclosed embodiments.

The term "biomarker", as used herein, refers to any protein that can be detected, directly or indirectly, e.g. via an analog, metabolite, fragment or breakdown product including post-translational modifications such as glycosylation, fucosylation, methylation and/or acetylation, in a biological sample from a subject. An alteration, such as an increase or decrease, of the amount of the biomarker as compared to amounts found in control subjects, such as subjects without disease or non-diseased tissue within the same subject, is indicative of the presence or risk of disease such as cancer, in a subject. The analog, metabolite, fragment or breakdown product of the biomarker may or may not possess the functional activity of the biomarker. The biomarkers of the present embodiments are platelet-derived biomarkers and are, thus, obtained from platelets in the biological sample from the subject.

The term "relative amount" (or only "amount") refers to the measured quantity of a given marker protein in relation to the measured quantity of a different marker protein. I.e. the term "relative amount" for a given marker protein is used to describe a normalized quantity (with reference to the quantity of a standard or as percentage of the total amount of all proteins in the sample), or in relation to the quantity of other proteins within a given panel of multiple marker proteins.

The terms "altered cells" or "altered tissue" refers to the presence or occurrence of a lesion or similar which might be either benign or malignant. The "occurrence of altered cells/altered tissue/lesions" as used herein refers to the occurrence of cells/tissue/lesions that are either benign or malignant. Prediction of such "altered cells/tissue/lesions" hence refers to the occurrence of such cells/tissue or lesions in a subject. Selected platelet-derived biomarkers of the embodiments could thus be used for predicting if a subject is healthy, or if the subject suffers from altered cells/tissue/lesions, i.e. suffers from benign and/or malignant lesions. The platelet-derived biomarkers, thus, discriminate between healthy individuals and individuals with the occurrence of some kind of benign or malignant lesions.

The term "cancer status" as used herein refers to defining the status as cancer, i.e. malign tumor tissue or lesions, or the status as no cancer, i.e. benign tissue or lesions, wherein the status could also be referred to as "disease status", for a patient with some kind of lesions. When dividing into benign and malignant, one could also use the term "tumor status". Furthermore, cancer status might also refer to the progression of a cancer, whether the cancer is early or advanced, i.e. at an early stage or at a later stage. Hence, the embodiments can be used for detecting cancer, i.e. discriminating between cancer and no cancer. No cancer might either be benign lesions or a fully healthy individual, depending on the context. The embodiments can also, or alternatively, be used for determining the progression of a cancer, if the cancer is at an early stage or at a late stage, hence determining the progression of a cancer as cancer status. The predicted cancer status may additionally be employed for improved prognosis and/or treatment of the subject.

The term "benign lesion" or "benign tissue" relates to a lesion or tissue consisting of non-dysplastic cells, it lacks the ability for invasive growth and metastatic spread. Benign lesions and tissues still produce negative health effects.

The terms "malignant lesions", or "cancer" is characterized by uncontrolled cell division, invasive growth, activation of angiogenesis, impaired mechanism of natural cell death, i.e. apoptosis, is built from anaplastic cells and forms distant malignant tumors called metastasis. Metastatic spread happens through the lymphatic system, blood vessels and by peeling off, like during ovarian cancer.

The term "healthy controls" or "HC" as used herein is equivalent to healthy subjects with no sign of ongoing infection or disease. Healthy controls have no benign or malignant lesions.

The term "controls" is herein include healthy controls or "benign controls" or "BC" having benign lesions.

The term "early stage" cancer refers to cancers that have not yet spread so much or have not yet heavily affected the subject suffering from said early cancer. Regarding carcinomas, i.e. epithelial cancers, including, for instance, ovarian cancer, prostate cancer, colorectal cancer and pancreas cancer, generally four (I-IV) grades or stages are used to classify the stage of the cancer and the cancer progression. Early stage carcinoma includes stage or grade I and II carcinoma. and "late stage" carcinoma includes stage or grade III and IV carcinoma.

The terms "advanced" cancer or "late stage" cancer refer to cancers that have spread or are heavily affecting the subject suffering from said advanced cancer. Regarding carcinomas, late stage carcinoma includes stage or grade III and IV carcinoma. Late stage cancer is sometimes also denoted as "spread" or "disseminated".

The term "local tumors" of epithelial ovarian cancer (EOC) or "LC" is often used equivalent to early stages of EOC, including stage I and II, and the term "spread tumors" of EOC or "SC" are often used equivalent to late stages EDO, including stage III and IV. Local cancer or tumor as used herein refers generally to cancer or tumor present in one locus in the subject's body. This tumor has preferably not spread to other loci in the subject's body. Spread or disseminated cancer or tumor is characterized by the presence of metastasis.

The term "carcinoma", i.e. epithelial cancer, refers to cancer that is believed to arise from the surface (epithelium) of a certain tissue. Such cancers include ovarian, prostate, colorectal and pancreatic cancers.

The terms "cancer diagnosis", "diagnosing" or "diagnosis" as used herein refer to providing an indication that a subject may be afflicted with a disease, e.g. cancer, such as ovarian cancer, prostate cancer, colorectal cancer or pancreatic cancer. It will be appreciated that no such technique is perfect and that such diagnosis may be confirmed by other procedures such as physical examination, imaging, histological examination of tissue samples, etc. A diagnosis could predict if a present lesion is benign or malignant. It could also diagnose subjects with cancer or no cancer, wherein no cancer might be either benign lesions or no lesions (healthy subject).

The term "cancer prediction" refers to predicting the likelihood that a subject tested has a cancer disease. A prediction could, for instance, be either cancer or no cancer. A prediction is typically never completely certain but produces a plausible scenario or indication.

The term "cancer treatment regimen" refers how the patient is treated for the disease or disorder present in view of procedures and medication (therapy). In this case, if the predicted cancer status for a subject is cancer an anti-cancer treatment regimen is selected for the subject. Non-limiting examples of such anti-cancer treatment regimens include chemotherapy, surgery and/or irradiation. If the cancer status predicted for the subject indicates no cancer (healthy or benign), generally no cancer treatment regimen is needed. In this embodiment selecting the treatment regimen comprises selecting an anti-cancer treatment regimen or no anti-cancer treatment regimen based on the cancer status.

As used herein, the terms "subject" and "patient" are used interchangeably. As used herein, a subject is an animal, preferably a mammal such as a non-primate, e.g., cows, pigs, horses, cats, dogs, rats, etc., or a primate, e.g., monkey, e.g., a rhesus monkey, a cynomolgus monkey or chimpanzee, and human, and most preferably a human.

The protein panels of the present embodiments may be used for determining the occurrence of benign and/or malignant lesions in a subject, discriminating between benign and malignant lesions in a subject and/or predicting cancer status in a subject, including predicting cancer stage of a malignant lesion in the subject. The occurrence of benign and/or malignant lesion in a subject could either be present, i.e.

subject suffering from benign and/or malignant lesion, or not present, i.e. healthy individual. The platelet-derived biomarkers could thus be used to discriminate between healthy subjects and subjects suffering from some kind of altered tissue, benign and/or malignant lesion(s).

Cancer status, for example refers, to defining the status of a present altered tissue as cancer, i.e. malignant lesion, or the status as no cancer, i.e. benign lesion. The platelet-derived biomarkers could thus be used to discriminate between subjects with benign lesions and subjects suffering from malignant lesions (cancer). This prediction of cancer status could also be referred to as cancer diagnosis, thus diagnosing a lesion of a subject as benign or malignant.

Furthermore, cancer status might also refer to the progression of a cancer, wherein the possible statuses are early or late stage cancer. The platelet-derived biomarkers could thus be used to discriminate between subjects with cancer in an early stage and subjects suffering from cancer in a late stage. This could also be referred to as prediction of cancer progression status.

Hence, the embodiments can be used for detecting cancer, i.e. discriminating between cancer and benign tissue (no cancer). The embodiments can also, or alternatively, be used for determining the progression of a cancer, if the cancer is in an early or late stage, hence determining the progression of a cancer as cancer status. The predicted cancer status may additionally be employed for improved prognosis and/or treatment of the subject.

A particular advantage of embodiments is to diagnose highly malignant cancers early, i.e. to determine if a subject with small or well-defined lesions is having benign lesion or early malignant lesions, and to be able to do this non-invasively. Such highly malignant cancers include ovarian cancer, pancreatic cancer and colorectal cancer. Also, to be able to diagnose prostate cancer without the need for biopsies is an advantage of embodiments.

The present embodiments provide specific proteome patterns in platelets useful in cancer diagnosis. The embodiments presented herein allow for a patient friendly detection, prediction and diagnosis of cancer based on a biological sample, such as blood sample or other platelet-containing biological sample. This patient friendly and easy way of obtaining information about the disease by using a biological sample is a great tool for cancer diagnostics without the need for tissue biopsies. The present embodiments will provide a minimal trauma and at the same time more accurate diagnostic procedure. Using, for instance, a blood sample instead of biopsies will also have the advantage that there is no risk of seeding cancer cells into the blood system, thus avoiding the risk that the diagnosis contributes to disease progression, and that the trauma patients may experience during sample collections of today is avoided.

Prior to discussing various embodiments, a short discussion of the various platelet-derived biomarkers, used in the embodiments follows herein.

ACTB, beta-actin is one of six different actin isoforms which have been identified in humans. This is one of the two non-muscle cytoskeletal actins. Actins are highly conserved proteins that are involved in cell motility, structure and integrity.

ACTN1, α.actinin 1 is encoded by the ACTN1 gene in humans. Alpha actinin is a cytoskeletal protein and an actin-binding proteins with multiple roles in different cell types. In non-muscle cells, the cytoskeletal isoform is found along microfilament bundles and adherence-type junctions, where it is involved in binding acting to the membrane.

ACTN4, α.actinin 4, Q96BG6, see general information of alpha actinins above for ACTN1.

AP4A, diadenosine tetraphosphate, also referred to as bis(5-nucleosyl)-tetraphosphatease, P50583, is a putative alarmone, ubiquitous in nature being common to everything from bacteria to humans. Adenosine polyphosphates are capable of inducing multiple physiological effects. The molecule's role as a second messenger has recently been discovered in the LysRS-Ap4A-MITF signaling pathway. It asymmetrically hydrolyzes Ap4A to yield AMP and ATP. Plays a major role in maintaining homeostasis. (Described in study 1C)

CASP3, caspase 3 is a member of the cysteine-aspartic acid protease (caspase) family. Sequential activation of caspases plays a central role in the execution-phase of cell apoptosis. Caspases exist as inactive proenzymes that undergo proteolytic processing at conserved aspartic residues to produce two subunits, large and small, that dimerize to form the active enzyme. This protein cleaves and activates caspases 6 and 7; and the protein itself is processed and activated by caspases 8, 9, and 10. CAZA1, F-actin capping protein subunit alpha-1, P52907, binds in a $Ca^{2+}$-independent manner to the fast growing ends of actin filaments (barbed end) thereby blocking the exchange of subunits at these ends. Unlike other capping proteins, such as gelsolin and severin, these proteins do not sever actin filaments.

CLF1, cofilin 1 is a widely distributed intracellular actin-modulating protein that binds and depolymerizes filamentous F-actin and inhibits the polymerization of monomeric G-actin in a pH-dependent manner. It is involved in the translocation of actin-cofilin complex from cytoplasm to nucleus.

CLU, clusterin, also referred to as apolipoprotein J, is a 75-80 kDa disulfide-linked heterodimeric protein associated with the clearance of cellular debris and apoptosis. This protein has several synonyms: dimeric acidic glycoprotein (DAG protein), testosterone repressed prostate message-2 (TRPM-2), sulfated glycoprotein-2 (SGP-2) and complement lysis inhibitor (CLI).

CNDP2, cytosol non-specific dipeptidase, Q96KP4, hydrolyzes a variety of dipeptides including L-carnosine but has a strong preference for Cys-Gly. Isoform 2 may be play a role as tumor suppressor in hepatocellular carcinoma (HCC) cells.

CRKL, crk-like protein, P46109, may mediate the transduction of intracellular signals. Mounting evidence indicates that dysregulation of Crk proteins is associated with human diseases, including cancer and susceptibility to pathogen infections.

ERP29, endoplasmic reticulum resident protein 29, P30040, plays an important role in the processing of secretory proteins within the endoplasmic reticulum (ER), possibly by participating in the folding of proteins in the ER. Sequence similarity to the protein disulfide-isomerase family, but does not seem to be a disulfide isomerase.

FERM, fermitin family member 3, also referred to as FERMT3, kindling-3, MIG2-like protein or unc-112-related protein 2, has the capacity and function to bind and activate the integrins. The fermitin family members have generally a role in cell adhesion, migration, differentiation and proliferation. FERM has a key role in the regulation of hemostasis and thrombosis. This protein may also help maintain the membrane skeleton of erythrocytes.

FIBG, firbrinogen gamma chain, or FGG, has a double function: yielding monomers that polymerize into fibrin and acting as a cofactor in platelet aggregation. The gamma component of fibrinogen, a blood-borne glycoprotein is one of three pairs of nonidentical polypeptide chains. Following vascular injury, fibrinogen is cleaved by thrombin to form fibrin which is the most abundant component of blood clots. In addition, various cleavage products of fibrinogen and fibrin regulate cell adhesion and spreading, display vasoconstrictor and chemotactic activities, and are mitogens for several cell types.

FLNA, filamin A, also referred to as filamin alpha and acting binding protein 280 (ABP-280), helps build the network of protein filaments (cytoskeleton) that gives structure to cells and allows them to change shape and move. FLNA binds to another protein called actin and helps it to form the branching network of filaments that make up the cytoskeleton. FLNA also links actin to many other proteins to perform various functions within the cell, including regulating skeletal and brain development, the formation of blood vessels, and blood clotting. Remodeling of the cytoskeleton is central to the modulation of cell shape and migration. FLNA is a widely expressed protein that regulates re-organization of the actin cytoskeleton by interacting with integrins, transmembrane receptor complexes and second messengers. In an embodiment FLNA is in the form of FLNA protein C-terminal.

FPPS, farnesyl pyrophosphate synthase is an enzyme that converts dimethylallylpyrophosphate and isopentenyl pyrophosphate into farnesylpyrophosphate. It is also referred to as farnesylpyrophosphate synthase or farnesyldiphosphate synthase.

GELS, gelsolin, also referred to as Actin-depolymerizing factor, P06396, is a calcium-regulated, actin-modulating protein that binds to the plus (or barbed) ends of actin monomers or filaments, preventing monomer exchange (end-blocking or capping). It can promote the assembly of monomers into filaments (nucleation) as well as sever filaments already formed. Gelsolin plays a role in ciliogenesis.

GPIX, glycoprotein IX, P14770. The GPIb-V-IX complex functions as the vWF receptor and mediates vWF-dependent platelet adhesion to blood vessels. The adhesion of platelets to injured vascular surfaces in the arterial circulation is a critical initiating event in hemostasis. GP-IX may provide for membrane insertion and orientation of GP-Ib. (Described in study 1C)

GRP75, mitochondrial stress-70 protein, also denoted mtHSP70 and HSPA9, is involved in the control of cell proliferation and cellular aging. It may also act as a chaperone.

GSTO1, glutathione S-transferase omega-1 is an enzyme that in humans is encoded by the GSTO1 gene. This gene encodes a member of the theta class glutathione S-transferase-like (GSTTL) protein family. In mouse, the encoded protein acts as a small stress response protein, likely involved in cellular redox homeostasis. This protein has dehydroascorbate reductase activity and may function in the glutathione-ascorbate cycle as part of antioxidant metabolism.

HDHD2, haloacid dehalogenase-like hydrolase domain-containing protein 2 is an enzyme that in humans is encoded by the HDHD2 gene.

HP protein, Q6NSB4, belongs to the peptidase S1 family. Sequence length is 281AA and AA 34-281 in HP protein corresponds to AA 159-406 in Haptoglobin (P00738).

HSP70, heat chock 70 kDa protein, Q53HF2, has ATP binding function. Heat-shock proteins (HSPs), or stress proteins, are highly conserved and present in all organisms and in all cells of all organisms. Selected HSPs, also known as chaperones, play crucial roles in folding/unfolding of proteins, assembly of multiprotein complexes, transport/sorting of proteins into correct subcellular compartments, cell-cycle control and signaling, and protection of cells against stress/apoptosis.

HSP71, heat shock protein 71 kDa protein.

HSP90AB1, heat shock protein HSP 90-beta is a protein that in humans is encoded by the HSP90AB1 gene.

ILEU, leukocyte elastase inhibitor, also referred to as LEI, P30740, regulates the activity of the neutrophil proteases elastase, cathepsin G, proteinase-3, chymase, chymotrypsin, and kallikrein-3. It also functions as a potent intracellular inhibitor of granzyme H.

ITGA2B (or ITA2B), Integrin alpha-IIb, also referred to as ITGA2B, platelet glycoprotein IIb (GPIIb) or CD41, P08514, is encoded by the ITGA2B gene in humans. Integrins are heterodimeric integral membrane proteins composed of an alpha chain and a beta chain, Integrin alpha-IIb/beta-3 is a receptor for fibronectin, fibrinogen, plasminogen, prothrombin, thrombospondin and vitronectin. Following activation integrin alpha-IIb/beta-3 brings about platelet/platelet interaction through binding of soluble fibrinogen. This step leads to rapid platelet aggregation which physically plugs ruptured endothelial cell surface.

ITB3, integrin beta-3, also referred to as Platelet glycoprotein IIIa (GPIIIa) or CD61), P05106. Integrins are heterodimeric integral membrane proteins composed of an alpha chain and a beta chain. Integrin alpha-V/beta-3 is a receptor for cytotactin, fibronectin, laminin, matrix metalloproteinase-2, osteopontin, osteomodulin, prothrombin, thrombospondin, vitronectin and von Willebrand factor. Integrin alpha-IIb/beta-3 is a receptor for fibronectin, fibrinogen, plasminogen, prothrombin, thrombospondin and vitronectin. Following activation integrin alpha-IIb/beta-3 brings about platelet/platelet interaction through binding of soluble fibrinogen. This step leads to rapid platelet aggregation which physically plugs ruptured endothelial surface.

ITGA6, integrin alpha-6. For more information of integrins see ITGA2B and ITB3 above.

KAP3, cAMP-dependent protein kinase subunit RII-beta, P31323, is a regulatory subunit of the cAMP-dependent protein kinases involved in cAMP signaling in cells. Type II regulatory chains mediate membrane association by binding to anchoring proteins, including the MAP2 kinase.

MLEC, malectin is a carbohydrate-binding protein of the endoplasmic reticulum and a candidate player in the early steps of protein N-glycosylation.

PHB, prohibitin, Q6PUJ7, is a protein that in humans is encoded by the PHB gene. Prohibitins are divided in two classes, termed Type-I and Type-II prohibitins, based on their similarity to yeast PHB1 and PHB2, respectively. Each organism has at least one copy of each type of prohibitin gene. PHB is thought to be a negative regulator of cell proliferation and may be a tumor suppressor.

RINI, ribonuclease inhibitor, P13489, inhibits RNASE1, RNASE2 and ANG. It may play a role in redox homeostasis.

SHLB1, endophilin-B1 isoform 1, Q9Y371, may be required for normal outer mitochondrial membrane dynamics. It is required for coatomer-mediated retrograde transport in certain cells. It may recruit other proteins to membranes with high curvature. SHLB1 may promote membrane fusion. The encoded protein interacts with the proapoptotic member of the Bcl-2 family, Bcl-2-associated X protein (Bax) and may be involved in regulating apoptotic signaling pathways. This protein may also be involved in maintaining mitochondrial morphology.

SNCA, alpha-synuclein interacts with phospholipids and proteins. Presynaptic terminals release chemical messengers, called neurotransmitters, from compartments known as synaptic vesicles. The release of neurotransmitters relays signals between neurons and is critical for normal brain function. It plays an important role in maintaining a supply of synaptic vesicles in presynaptic terminals. It may also help regulate the release of dopamine, a type of neurotransmitter that is critical for controlling the start and stop of voluntary and involuntary movements.

SPB6, serpin B6 is a protein that in humans is encoded by the SERPINB6 gene. It may be involved in the regulation of serine proteinases present in the brain or from the blood. It is an inhibitor of cathepsin G, kallikrein-8 and thrombin. SPB6 may play an important role in the inner ear in the protection against leakage of lysosomal content during stress and loss of this protection results in cell death and sensorineural hearing loss.

SRC, proto-oncogene tyrosine-protein kinase Src, P12931, participates in signaling pathways that control a diverse spectrum of biological activities including gene transcription, immune response, cell adhesion, cell cycle progression, apoptosis, migration, and transformation.

TBA, tubulin highly similar to tubulin alpha-ubiquitous chain, B3KPS3. Tubulin is one of several members of a small family of globular proteins. The tubulin superfamily includes five distinct families, the alpha-, beta-, gamma-, delta-, and epsilon-tubulins. The most common members of the tubulin family are α-tubulin and β-tubulin, the proteins that make up microtubules. Each has a molecular weight of approximately 55 kiloDaltons. Microtubules are assembled from dimers of α- and β-tubulin. These subunits are slightly acidic with an isoelectric point between 5.2 and 5.8. To form microtubules, the dimers of α- and β-tubulin bind to GTP and assemble onto the (+) ends of microtubules while in the GTP-bound state.[4] The β-tubulin subunit is exposed on the plus end of the microtubule while the α-tubulin subunit is exposed on the minus end. After the dimer is incorporated into the microtubule, the molecule of GTP bound to the β-tubulin subunit eventually hydrolyzes into GDP through inter-dimer contacts along the microtubule protofilament. Whether the β-tubulin member of the tubulin dimer is bound to GTP or GDP influences the stability of the dimer in the microtubule. Dimers bound to GTP tend to assemble into microtubules, while dimers bound to GDP tend to fall apart; thus, this GTP cycle is essential for the dynamic instability of the microtubule.

TBA4A, tubulin alpha-4A chain, P68336, see TBA above.

THTM, 3-mercaptopyruvate sulfurtransferase, also referred to as MPST, TST2, and Rodanese, P5325, transfers a sulfur ion to cyanide or to other thiol compounds. It also has weak rhodanese activity. THTM detoxifies cyanide and is required for thiosulfate biosynthesis. It acts as an antioxidant. In combination with cysteine aminotransferase (CAT), it contributes to the catabolism of cysteine and is an important producer of hydrogen sulfide in the brain, retina and vascular endothelial cells. Hydrogen sulfide $H_2S$ is an important synaptic modulator, signaling molecule, smooth muscle contractor and neuroprotectant. Its production by the 3MST/CAT pathway is regulated by calcium ions.

TLN1, talin1, Q9Y490, is probably involved in connections of major cytoskeletal structures to the plasma membrane. It is a high molecular weight cytoskeletal protein concentrated at regions of cell-substratum contact and, in lymphocytes, at cell-cell contacts.

TPM1, tropomysin alpha-1, F5H7S3. The tropomyosins is widely distributed actin-binding proteins.

TSG, tumor susceptibility gene 101 protein belongs to a group of apparently inactive homologs of ubiquitin-conjugating enzymes. The protein contains a coiled-coil domain that interacts with stathmin, a cytosolic phosphoprotein implicated in tumorigenesis. The protein may play a role in cell growth and differentiation and act as a negative growth regulator.

TUBB1 tubulin beta 1, also referred to as class VI and class VI beta-tubulin, QH4B7, is encoded by the TUBB1 gene in humans. β-Tubulins are one of two core protein families that heterodimerize and assemble to form microtubules. Microtubules are involved in a wide variety of cellular processes, including mitosis, morphogenesis, platelet formation and mobility of cilia and flagella. This protein is specifically expressed in platelet and megakaryocytes and may be involved in proplatelet production and platelet release.

VCL, vinculin is encoded by the VCL gene in humans. VCL is a cytoskeletal protein associated with cell-cell and cell-matrix junctions and may play important roles in cell morphology and locomotion.

WDR1, WD repeat-containing protein 1, is encoded by the WDR1 gene in humans. WDR1 generally contains 9 WD repeats. Such WD repeats are approximately 30 to 40 amino acids domains containing several conserved residues. WD domains are generally involved in protein-protein interaction. WDR1 may help to induce the disassembly of actin filaments.

An aspect of the embodiments relates to a method of determining whether a subject is suffering from a benign lesion or from a carcinoma lesion. The method comprises measuring at least two platelet-derived biomarkers in a biological sample from the subject. In this aspect, the least two platelet derived biomarkers are selected from a group consisting of ACTN1, ACTN4, CRKL, ERP29, FERM, FIBG, FLNA, GELS, GRP75, HP protein, HSP70, HSP71, ITGA2B, ITB3, RINI, SRC, TBA, TBA4A, THTM, TLN1, TUBB1, VCL and WDR1. The method also comprises determining whether the subject is suffering from the benign lesion or from the carcinoma lesion based on the measurement.

Hence, the platelet-derived biomarkers listed in the above presented group or panel can be used to discriminate whether a subject is suffering from a benign lesion or from a carcinoma lesion. This means that these platelet-derived biomarkers can be used for those subjects having a lesions, i.e. altered cells or tissue, in order to verify or at least predict whether the lesion is benign, i.e. generally less harmful, or carcinoma, i.e. malignant.

In an embodiment, the method comprises determining whether the subject is suffering from the benign lesion or from an ovarian or prostate cancer lesion based on the measurement.

In this embodiment, the above presented group of panel of platelet-derived biomarkers are particular suitable for use in diagnosing ovarian or prostate cancer lesions as preferred examples of carcinoma lesions.

As is further disclosed herein, experimental data suggest that some of the listed platelet-derived biomarkers may be more important than other platelet-derived biomarkers in the determination of lesions type, i.e. benign vs. carcinoma or malignant. The six most important such platelet-derived biomarkers include ERP29, ACTN4, HP-protein, TLN1, SRC and THTM. In such an embodiment, the method preferably comprises measuring, in the biological sample, at least two platelet-derived biomarkers selected from a group consisting of ERP29, ACTN4, HP-protein, TLN1, SRC and THTM.

Thus, it is in particular platelet-derived biomarkers from this limited group that provide the most significant information with regard to classifying lesions as benign or carcinoma.

In an alternative approach, each platelet-derived biomarker that is measured in the method could have an associated weight value that is determined based on and represents the importance of that particular platelet-derived biomarker in the diagnosis. Such weights could be determined based on the VIP (variable of importance) ranks listed for these platelet-derived biomarkers further below.

In an embodiment, the method comprises measuring a respective amount of the at least two platelet-derived biomarkers in the. The method also comprises comparing the respective amount with a respective control amount representing an amount of the respective platelet-derived biomarker in a biological sample from a control subject. The method further comprises determining whether the subject is suffering from the benign lesion or from the carcinoma lesion based on the comparison.

Thus, in this embodiment a respective control amount is preferably determined for each platelet-derived biomarker to be measured. The control subject could be a subject diagnosed as suffering from a benign lesion but lacks any carcinoma lesions. Alternatively, the control subject could be a subject diagnosed as suffering from a carcinoma lesion but lacks any benign lesions. The profile of platelet-derived biomarkers measured in the biological sample from the subject is then compared to the control profile of the control subject in order to determine whether the profile matches control profile. Such a comparison can then be used to classify any lesions in the subject.

In a particular embodiment, the method comprises determining whether the subject is suffering from the benign lesion or from an early stage carcinoma lesion based on the measurement.

Thus, in a preferred embodiment the method can be used to discriminate between relative harmless benign lesions and early stage carcinoma lesions. It is generally, with the prior art techniques, very hard to make such a distinction between benign lesions and early sage carcinoma lesions, i.e. prior to the formation of any metastases or at least significant spread of the carcinoma. The embodiment therefore will be a valuable tool in early cancer detection to differentiate relative harmless benign lesions from carcinoma lesions already prior to metastasis.

Another aspect of the embodiments relates to a method of predicting existence of a benign and/or carcinoma lesion in a subject. The method comprises measuring at least two platelet-derived biomarkers in a biological sample from the subject. In this aspect, the at least two platelet derived biomarkers are selected from a group consisting of AP4A, CAZA1, CNDP2, GPIX, ILEU, KAP3, PHB, SHLB1, SPB6 and TMP1. The method also comprises predicting existence of the benign and/or carcinoma lesion in the subject based on the measurement.

The platelet-derived biomarkers in this second group or panel are suitable to differentiate between healthy subjects, i.e. lacking any benign or carcinoma, i.e. malignant, lesions, and subjects that have benign lesions, have carcinoma lesions or have both benign and carcinoma lesions.

This method may advantageously be used as an initial screening to detect any lesions and then be complemented by the previously described aspect to classify whether any detected lesion is benign or carcinoma.

In an embodiment, the method comprises predicting existence of a benign and/or ovarian or prostate cancer lesion in the subject based on the measurement. Thus, this method and the listed platelet-derived biomarkers are particularly suitable for use in connection with ovarian or prostate cancer as examples of carcinomas.

In an embodiment, the method comprises measuring a respective amount of the at least two platelet-derived biomarkers in the biological sample. The method also comprises comparing the respective amount with a respective control amount representing an amount of the respective platelet-derived biomarker in a biological sample from a control subject. The method further comprises predicting existence of the benign and/or carcinoma lesion in the subject based on the comparison.

In this embodiment, the control subject is preferably a healthy subject, i.e. a subject lacking any benign or carcinoma lesions. The comparison is preferably performed similar to what has been discussed in the foregoing using a comparison of profiles of platelet-derived biomarkers.

A further aspect of the embodiments relates to a method of predicting existence of colorectal or pancreas cancer in a subject. The method comprises measuring at least two platelet-derived biomarkers in a biological sample from the subject. In this aspect, the at least two platelet derived biomarkers are selected from a group consisting of CTB, ACTN1, CASP3, CLF1, CLU, FPPS, GELS, GSTO1, HSP90AB1, HDHD2, ITGA2B, ITB3, ITGA6, MLEC, PHB, RINI, SNCA, SPB6, TBA4A, TLN1, TSG, TBB1, VCL and WDR1. The method also comprises predicting existence of the colorectal or pancreas cancer in the subject based on said measurement.

This method and the listed platelet-derived biomarkers can thereby be used to diagnose subjects as suffering from colorectal or pancreas cancer as preferred examples of carcinomas. The platelet-derived biomarkers can thereby be used to differentiate between healthy subjects, i.e. no benign or carcinoma lesions, and subjects with benign lesions from subject suffering from colorectal or pancreas cancer.

In an embodiment, the method comprises measuring, in the biological sample, the at least two platelet-derived biomarkers selected from a group consisting of ACTB, ACTN1, CAPS3, CFL1, CLU, FPPS, GELS, GSTO1, HDHD2, ITGA2B, ITB3, ITGA6, MLEC, PHB, RINI, SNCA, SPB6, TBA4A, TLN1, TSG, TUBB1, VCL and WDR1. The method also comprises predicting existence of the colorectal cancer in the subject based on the measurement.

In another embodiment, the method comprises measuring, in the biological sample, the at least two platelet-derived biomarkers selected from a group consisting of ACTB, ACTN1, CAPS3, CFL1, CLU, FPPS, GELS, HSP90AB1, HDHD2, ITGA2B, ITB3, ITGA6, MLEC, PHB, RINI, SNCA, SPB6, TBA4A, TLN1, TSG, TUBB1, VCL and WDR1. The method also comprises predicting existence of the pancreas cancer in the subject based on the measurement.

Thus, of the previously listed group of platelet-derived biomarkers that can be used in the present embodiment, 22 are common for both colorectal cancer and pancreas cancer. Furthermore, the platelet-derived biomarker HSP90AB1 seems to be unique for pancreas cancer, whereas GSTO1 seems to be unique for colorectal cancer.

In an embodiment, the method comprises measuring a respective amount of the at least two platelet-derived biomarkers in the biological sample. The method also comprises comparing the respective amount with a respective control amount representing an amount of the respective platelet-derived biomarker in a biological sample from a control subject. The method further comprises predicting existence of the colorectal or pancreas cancer in the subject based on the comparison.

In this embodiment, the control subject is preferably a healthy subject, i.e. a subject lacking any benign or carcinoma lesions, or a subject having benign lesions but lacking any carcinoma lesions. Alternatively, the control subject could be a subject diagnosed as suffering from colorectal or pancreas cancer. The comparison is preferably performed similar to what has been discussed in the foregoing using a comparison of profiles of platelet-derived biomarkers.

Yet another aspect of the embodiments relates to a method of predicting existence of carcinoma in a subject. The method comprises measuring at least two platelet-derived biomarkers in a biological sample from the subject. In this aspect, the at least two platelet derived biomarkers are selected from a group consisting of ACTN1, GELS, ITGA2B, ITB3, PHB, RINI, SPB6, TBA4A, TLN1, TBB1, VCL and WDR1. The method also comprises predicting existence of the carcinoma in the subject based on the measurement.

The above listed panel or group of platelet-derived biomarkers can thereby be used to detect early stage carcinoma in a subject, i.e. detect any such cancer tumors at a very early stage (stage I or II) and prior to metastasis. In such a case, the method comprises predicting existence of an early stage carcinoma in the subject based on the measurement.

Such a detection of early stages of carcinomas are particularly advantageous according to the embodiments. Hence, it is with this method possible to detect carcinomas in a subject prior to extensive metastasis and when the cancer is preferably still limited to a single locus. The reason being that cancer treatment is much more successful if the treatment is initiated for an early stage cancer as compared to treating a late stage cancer.

In a particular embodiment, the method comprises predicting existence of an epithelial cancer in the subject based on the measurement, preferably predicting existence of an early stage epithelial cancer in the subject based on the measurement.

Currently preferred examples of such carcinomas and epithelial cancers include ovarian cancer, prostate cancer, colorectal cancer and pancreas cancer.

In an embodiment, the method comprises measuring a respective amount of said at least two platelet-derived biomarkers in the biological sample. The method also comprises comparing the respective amount with a respective control amount representing an amount of the respective platelet-derived biomarker in a biological sample from a control subject. The method further comprises predicting existence of the carcinoma in the subject based on the comparison.

The control subject is preferably a healthy subject or a subject suffering from benign lesions. The comparison is preferably performed similar to what has been discussed in the foregoing using a comparison of profiles of platelet-derived biomarkers.

The biological sample in which the at least two platelet-derived biomarkers are measured could be any biological sample comprising platelets. Biological sample as used herein refers to any material taken from the body of a subject that may carry the target compound or compounds of the tests described herein, including both tissue samples and biological fluids such as blood samples, saliva samples, urine samples, etc. In a representative embodiment, a biological sample is a blood sample, an extracted platelet sample, and the like. Blood sample as used herein refers to whole blood or any fraction thereof (e.g. blood plasma, blood serum) that may contain detectable levels of platelet-derived biomarkers therein (if the biomarkers are present in the whole blood sample from which said fraction is obtained), and in particular embodiments refers to a blood plasma sample or a blood platelet sample.

In a particular example embodiment the method comprises the following steps:
 a) isolating platelets from a biological sample, preferably a blood sample, of the subject;
 b) extracting platelet-proteins from the platelets isolated in a);
 c) separating the platelets-proteins extracted in b) on a two-dimensional gel electrophoreses (2-DE) gel;
 d) identifying the at least two platelet-derived biomarkers on the 2-DE gel; and
 e) measuring an amount of the at least two platelet-derived biomarkers identified in d) on the 2-DE gel.

In a particular embodiment the isolating step a) comprises one or more, typically three centrifugation steps. In a first centrifugation step a blood sample is centrifuged to form a pellet of erythrocytes and plasma. This centrifugation step can be omitted if the biological sample is a plasma sample. The plasma is centrifuged in a second centrifugation step to form a pellet and a platelet-poor plasma. In an optional embodiment the platelet-rich pellet is resuspended and washed and subject to a third centrifugation step to form a pure platelet-rich pellet and a supernatant that is discarded.

The extraction of the platelet-proteins from the platelets in step b) can be performed according to well known lysis and extraction procedure, typically using a lysis buffer. The resulting platelet protein lysate is preferably subject to a centrifugation step to form a supernatant with platelet proteins and a waste pellet.

Step c) preferably performs a 2-DE that separates platelet proteins based on isoelectric point and mass. Thus, a first separation step is isolectric focusing where the platelet proteins are separated based on their isoelectric point. A second separation step separates the platelet proteins based on their molecular weight or mass using SDS-PAGE.

The platelet proteins on the 2-DE gel can be marked in step d) to enable identification of the relevant platelet-derived biomarker(s) and the subsequent measurement of the amount of the platelet-derived biomarker(s) in step e). Various protein marking protocols and methods can be used, such as silver staining. In such a case, the silver staining is preferably performed using a mass spectrometry compatible staining protocol. The stained platelet-derived biomarkers can then be scanned and the respective amount of the at least two platelet-derived biomarkers can be determined from the images of the stained 2-DE gel in step e).

Variants of the method steps a) to e) are possible and within the scope of the embodiments. For instance, antibodies specifically binding to the respective at least two platelet-derived biomarkers could be used for identifying and quantifying the relevant biomarker(s). Enzyme-linked immunosorbent assay (ELISA), mass spectrometry, a panel test (such as a multiplex Luminex® microsphere test) and multiple reaction monitoring (MRM) are examples of alternative or additional techniques that can be used instead of or as a complement to 2-DE. One such alternative embodiment is described below.

In a particular example embodiment the method comprises the following steps:
a) isolating platelets from a biological sample, preferably a blood sample, of the subject;

b) extracting platelet-proteins from the platelets isolated in a);

c) applying the extracted platelet-proteins from b); to an antibody based assay platform, said assay platform including antibodies towards the at least two biomarkers d) measuring the signal from the assay from c); in a diagnostic instrument, analyzing the measured signal using an algorithm and presenting the outcome for diagnostic evaluation In a particular embodiment the isolating step a) comprises one or more, typically three centrifugation steps. In a first centrifugation step a blood sample is centrifuged to form a pellet of erythrocytes and plasma. This centrifugation step can be omitted if the biological sample is a plasma sample. The plasma is centrifuged in a second centrifugation step to form a pellet and platelet-poor plasma. In an optional embodiment the platelet-rich pellet is resuspended and washed and subject to a third centrifugation step to form a pure platelet-rich pellet and a supernatant that is discarded.

The extraction of the platelet-proteins from the platelets in step b) can be performed according to well known lysis and extraction procedure, typically using a lysis buffer. The resulting platelet protein lysate is preferably subject to a centrifugation step to form a supernatant with platelet proteins and a waste pellet.

Step c) preferably perform a multiplex assay type ELISA (or Luminex) based on antibodies that have been raised specifically against the biomarkers used in a specific panel to fit the selected assay type. The panel should consist of antibodies towards the at least two biomarkers selected.

Step d) a quantitative read-out of the signal from the binding interaction between the antibodies and the biomarkers within the platelet-proteins from b); is done in an instrument. The signal can be from a generated fluorescent signal, a color developed based on an enzymatic reaction or other biological reporting system. The signal is then processed in the instrument and more specifically it's software using an algorithm as specified for the selected biomarker panel. The result of the processed signal is then given a value of between 0-1. The value will then be judged based on value-levels decided for each biomarker panel, the panels used within a specific cancer diagnosis and the diagnosis of a specific type of cancer. The algorithm is generated by a given PLS model (using appropriate multivariate software, e.g. SIMCA P v13, Umetrics AB) and will provide prediction scores between 0-1 according to a procedure which is well known for a scientist skilled in the art of PLS modelling (for an example, se: Ottervald J., et al., Multiple Sclerosis: Identification and clinical evaluation of novel CSF biomarkers, J Proteomics. 2010. Apr. 18: 73 (6): 1117-1132.) The prediction model provides for each new sample a value between 0 and 1, where values >0.5 indicate cancer and values <0.5 indicate benign lesions.

Panel test or multivariate assay refers to a group of individual laboratory tests that are related in some way, including, but not limited to, the medical condition they are designed to detect (e.g. cancer), the specimen type (e.g. blood), and the methodology employed by the test (e.g. detection of altered level of biomarker protein or proteins).

In a particular example embodiment the method comprises the following steps:

a) isolating platelets from a biological sample, preferably a blood sample, of the subject;

b) extracting platelet-proteins from the platelets isolated in a);

c) measuring an amount of the at least two platelet-derived biomarkers using a respective antibody that specifically binds to a respective platelet-derived biomarker of the at least two platelet-derived biomarkers.

The present embodiments can be used as an objective tool employed for non-invasive cancer diagnosis, clinical diagnosis of suspected cancers and hereditary indications, for follow-up of treatment of the cancer and for monitoring of potential recurrence, and for screening. The diagnostic method can also potentially be used as a Companion Diagnostic together with current and future treatment regimes and for early screening. The tool could be used for detection of lesions that might be malignant, (discriminating between healthy subjects and subject with benign or malignant lesions) for prediction/determination/evaluation of cancer status and/or prediction/determination/evaluation of cancer progression status.

It is a particular advantage of the embodiments to enable prediction of cancer status in a subject, i.e. to allow early diagnosis of cancer—before metastases can be detected, and to exclude benign lesions.

A further advantage of the embodiments is to detect or predict the occurrence of possible malignant lesions in a subject. Another advantage is to predict cancer (tumor) status/disease status (benign or malign lesions) in a subject with the occurrence of possible malignant lesions. A yet further advantage is to predict the cancer status in forms of cancer progression, determining if a subject with a malignant cancer are in an early or late stage of the disease. In a particular embodiment, lesions are present in the subject, but are so small or well localized that they are hard to distinguish as benign lesions or early malignant lesions (tumors). Instead of the hazardous procedure of taking a biopsy, the non-invasive procedure of the embodiments could be used, enabling discrimination between benign lesions and early malignant lesions (tumors), thus performing diagnosis of malignant cancer in an early stage.

A particular advantage of the embodiments is to be able to diagnose early stages of highly malignant cancer, such as ovarian-, pancreatic- and colorectal cancer, which are more or less incurable if diagnoses at a later stage. A further advantage is to perform such diagnosis without the need for invasive methods, such as taking biopsies. In particular, epithelial cancers are diagnosed, including ovarian, prostate, colorectal and pancreatic cancers. Panels of platelet-derived biomarkers are instead used, and by analyzing the expression of two or more of these markers, the malignancy of the lesion can be predicted/diagnosed.

The particular advantage is to diagnose highly malignant cancers early, i.e. to determine if a subject with small or well-defined lesions is having benign lesion or early malignant lesions, and to be able to do this non-invasively. Such highly malignant cancers include ovarian cancer, pancreatic cancer and colorectal cancer. Also, to be able to diagnose prostate cancer without the need for biopsies is an advantage of the current embodiments.

The present embodiments provide specific proteome patterns in platelets useful for detecting the occurrence of altered benign or malign cells/tissue/lesions, cancer status prediction, diagnosis of cancer as well as for discriminating between early cancer and advanced cancer. The embodiments presented herein allow for a patient friendly detection, prediction and diagnosis of cancer based on a blood sample or other platelet-containing biological sample. This patient friendly and easy way of obtaining information about the disease by using a biological sample, such as a blood sample, is a great tool for cancer diagnostics without the need for tissue biopsies. The present embodiments will provide a minimal trauma and at the same time more accurate diagnostic procedure. Using, for instance, a blood sample instead of biopsies will also have the advantage that there is no risk of seeding cancer cells into the blood system, thus avoiding the risk that the diagnosis contributes to disease progression, and that the trauma patients may experience during sample collections of today is avoided.

The at least two platelet-derived biomarkers of the embodiments are preferably at least two proteins derived from platelets present in the biological sample. In a particular embodiment, the at least two proteins are non-angiogenetic proteins derived from, i.e. obtainable from, platelets. In a particular embodiment the platelet-derived biomarkers are selected from a panel or group consisting of the following proteins ACTB, ACTN1, ACTN4, AP4A, CASP3, CAZA1, CFL1, CLU, CNDP2, CRKL, ERP29, FERM, FIBG, FLNA, FPPS, GELS, GPIX, GRP75, GSTO1, HDHD2, HP protein, HSP70, HSP71, HSP90AB1, ILEU, ITGA2B, ITB3, ITGA6, KAP3, MLEC, PHB, RINI, SHLB1, SNCA, SPB6, SRC, TBA, TBA4A, THTM, TLN1, TMP1, TSG, TUBB1, VCL and WDR1.

When predicting the occurrence of altered cells/tissue/lesions, i.e. benign and/or malignant, in particular carcinoma, lesions, which might potentially be malignant in ovarian and prostate cancer, the at least two biomarkers should be selected from the group consisting of AP4A, CAZA1, CNDP2, GPIX, ILEU, KAP3, PHB, SHLB1, SPB6 and TMP1.

When predicting cancer status relating to cancer occurrence, i.e. determining if the present lesions are benign or malignant, or when predicting cancer status relating to cancer progression (determining if the carcinoma is in an early or advanced stage), i.e. when diagnosing ovarian- or prostate cancer, the at least two platelet-derived biomarkers are selected from a group consisting of the following proteins: ACTN1, ACTN4, CRKL, ERP29, FERM, FIBG, FLNA, GELS, GRP75, HP protein, HSP70, HSP71, ITGA2B, ITB3, RINI, SRC, TBA, TBA4A, THTM, TLN1, TUBB1, VCL and WDR1.

When diagnosing pancreatic cancer, cancer or no cancer (healthy), the at least two platelet-derived biomarkers are selected from a group consisting of the following proteins ACTB, ACTN1, CASP3, CFL1, CLU, FPPS, GELS, HSP90AB1, HDHD2, ITGA2B, ITB3, ITGA6, MLEC, PHB, RINI, SNCA, SPB6, TBA4A, TLN1, TSG, TUBB1, VCL and WDR1.

When diagnosing colorectal cancer, cancer or no cancer (healthy), the at least two platelet-derived biomarkers are selected from a group consisting of the following proteins ACTB, ACTN1, CASP3, CFL1, CLU, FPPS, GELS, GSTO1, HDHD2, ITA2B, ITB3, ITGA6, MLEC, PHB, RINI, SNCA, SPB6, TBA4A, TLN1, TSG, TUBB1, VCL and WDR1.

There is also a panel of twelve platelet-derived biomarkers, which could be used irrespective of the cancer to be diagnosed. Thus, colorectal, ovarian, pancreatic and prostate cancer could be diagnosed using said panel, which consist of ACTN1, GELS, ITGA2B, ITB3, PHB, RINI, SPB6, TBA4A, TLN1, TUBB1, VCL and WDR1. When diagnosing pancreatic- and/or colorectal cancer, a panel of 22 markers has been found to be identical, whereas two pancreatric specific markers and two colorectal specific markers have been found. The panel of markers suitable for diagnosing both colorectal and pancreatic cancer is ACTB, ACTN1, CASP3, CFL1, CLU, FPPS, GELS, HDHD2, ITGA2B, ITB3, ITGA6, MLEC, PHB, RINI, SNCA, SPB6, TBA4A, TLN1, TSG, TUBB1, VCL and WDR1. When diagnosing only pancreatic cancer, a panel of 23 biomarkers could be used consisting of ACTB, ACTN1, CASP3, CFL1, CLU, FPPS, GELS, HSP90AB1, HDHD2, ITGA2B, ITB3, ITGA6, MLEC, PHB, RINI, SNCA, SPB6, TBA4A, TLN1, TSG, TUBB1, VCL and WDR1. When diagnosing only colorectal cancer, a panel of 23 biomarkers could be used consisting of ACTB, ACTN1, CASP3, CFL1, CLU, FPPS, GELS, GSTO1, HDHD2, ITGA2B, ITB3, ITGA6, MLEC, PHB, RINI, SNCA, SPB6, TBA4A, TLN1, TSG, TUBB1, VCL and WDR1.

Hence, there are several biomarker panels in the scope of the embodiments. One biomarker panel of 12 biomarkers is applicable for determining cancer status regardless of type of cancer. This panel consists of ACTN1, GELS, ITGA2B, ITB3, PHB, RINI, SPB6, TBA4A, TLN1, TUBB1, VCL and WDR1. Another biomarker panel of 10 biomarkers discriminates between healthy subjects and subjects with lesions (benign or malignant) in ovarian and/or prostate cancer and consists of AP4A, CAZA1, CNDP2, GPIX, ILEU, KAP3, PHB, SHLB1, SPB6 and TMP1. A further biomarker panel of 23 biomarkers for predicting cancer status (benign vs malignant or early vs advanced) in ovarian or prostate cancer consists of ACTN1, ACTN4, CRKL, ERP29, FERM, FIBG, FLNA, GELS, GRP75, HP protein, HSP70, HSP71, ITGA2B, ITB3, RINI, SRC, TBA, TBA4A, THTM, TLN1, TUBB1, VCL and WDR1. A further panel of 22 biomarkers may be used for predicting colorectal and/or pancreatic cancer status and consists of ACTB, ACTN1, CASP3, CFL1, CLU, FPPS, GELS, HDHD2, ITGA2B, ITB3, ITGA6, MLEC, PHB, RINI, SNCA, SPB6, TBA4A, TLN1, TSG, TUBB1, VCL and WDR1. For only predicting colorectal cancer status a panel of 23 biomarkers could be used, the panel of 22 biomarkers mentioned above supplemented with the biomarker GSTO1, and for predicting only pancreatic cancer status a panel of 23 biomarkers could be used, the panel of 22 biomarkers mentioned above supplemented with the biomarker HSP90AB1.

In an embodiment, two platelet-derived biomarkers of the relevant group or panel is measured in the respective method. In other embodiments more than two platelet-derived biomarkers are measured, such as 3, 4, 5, 6, 7, 8, 9, 10, 11, 12, 13, 14, 15, 16, 17, 18, 19, 20, 21 or 23 (depending on the number of platelet-derived biomarkers in respective group) platelet-derived biomarkers, including all or at least a major portion of the platelet-derived biomarkers in respective group.

For predicting the occurrence of benign and/or carcinoma, such as ovarian or prostate, lesions in a subject, the number of platelet-derived biomarkers measured could be any number ranging from at least two to at least 10 biomarkers, such as 2, 3, 4, 5, 6, 7, 8, 9 or 10biomarkers out of AP4A, CAZA1, CNDP2, GPIX, ILEU, KAP3, PHB, SHLB1, SPB6 and TMP1.

For predicting the cancer status in a subject suffering from ovarian or prostate cancer, the number of platelet-derived biomarkers measured could be any number ranging from at least two to at least 23 biomarkers, such as 2, 3, 4, 5, 6, 7, 8, 9, 10, 11, 12, 13, 14, 15, 16, 17, 18, 19, 20, 21, 22 or 23 biomarkers out of ACTN1, ACTN4, CRKL, ERP29, FERM, FIBG, FLNA, GELS, GRP75, HP protein, HSP70, HSP71, ITGA2B, ITB3, RINI, SRC, TBA, TBA4A, THTM, TLN1, TUBB1, VCL and WDR1.

For predicting the cancer status in a subject suffering from pancreatic cancer, the number of platelet-derived biomarkers measured could be any number ranging from at least two to at least 23 biomarkers, such as 2, 3, 4, 5, 6, 7, 8, 9, 10, 11, 12, 13, 14, 15, 16, 17, 18, 19, 20, 21, 22 or 23 biomarkers out of ACTB, ACTN1, CASP3, CFL1, CLU, FPPS, GELS, HSP90AB1, HDHD2, ITGA2B, ITB3, ITGA6, MLEC, PHB, RINI, SNCA, SPB6, TBA4A, TLN1, TSG, TUBB1, VCL and WDR1.

For predicting the cancer status in a subject suffering from colorectal cancer, the number of platelet-derived biomarkers measured could be any number ranging from at least two to at least 23 biomarkers, such as 2, 3, 4, 5, 6, 7, 8, 9, 10, 11, 12, 13, 14, 15, 16, 17, 18, 19, 20, 21, 22 or 23 biomarkers out of ACTB, ACTN1, CASP3, CFL1, CLU, FPPS, GELS, GSTO1, HDHD2, ITGA2B, ITB3, ITGA6, MLEC, PHB, RINI, SNCA, SPB6, TBA4A, TLN1, TSG, TUBB1, VCL and WDR1.

For predicting the cancer status in a subject suffering from pancreatic, ovarian, colorectal or prostate cancer, the number of platelet-derived biomarkers measured could be any number ranging from at least two to at least 12 biomarkers, such as 2, 3, 4, 5, 6, 7, 8, 9, 10, 11 or 12 biomarkers out of ACTN1, GELS, ITGA2B, ITB3, PHB, RINI, SPB6, TBA4A, TLN1, TUBB1, VCL and WDR1.

Any of these embodiments may be combined with measuring at least one other biomarker, preferably at least one other platelet-derived biomarker. The prediction of cancer status is then preferably based on the measured amounts of the at least two platelet-derived biomarkers of the embodiments and the measured amount(s) of the at least one other biomarker.

The present embodiments are particularly applicable to carcinomas. Hence, the cancer is advantageously a carcinoma or epithelial cancer. Preferred examples of cancer types to which the embodiments can be applied include ovarian cancer and/or prostate cancer. In such a case, the cancer status could be presence of ovarian cancer (or prostate cancer) versus no ovarian cancer (or no prostate cancer), i.e. only benign lesions, or advanced ovarian cancer (or advanced prostate cancer) versus early ovarian cancer (or early prostate cancer). Also, the presence of altered cells/tissue (lesions) in a subject could be predicted, classifying the subject as a healthy individual or one with altered cells/tissue (benign or malignant lesions). The embodiments could also be applied for pancreatic or colorectal cancer, discriminating between cancer and no cancer, benign or malignant lesions/tumors.

The method of the invention comprises measuring one or several biomarkers from a panel of biomarkers according to the invention. Preferably, at least two, or more, biomarkers are measured. The biomarkers might contribute differentially, and when listed, the VIP values might be used. The one with the highest VIP ranking will contribute the most and then it is descending. Depending on the amount of markers used in the prediction, the reliability of the prediction augments. Thus, the number of markers used might be selected based on the desired reliability of the prediction.

Another aspect of the embodiments relates to a method of selecting a cancer treatment regimen for a subject or patient, preferably a mammalian subject and more preferably a human subject. The method comprises determining whether the subject is suffering from a benign lesion or from a carcinoma lesion according to above; predicting existence of a benign and/or carcinoma lesion in said subject according to above; predicting existence of colorectal or pancreas cancer in said subject according to above; or predicting existence of carcinoma in said subject according to above. The method also comprises selecting treatment regimen for the subject based on whether the subject is suffering from the benign lesion or from the carcinoma lesion; based on the predicted existence of the benign and/or carcinoma lesion in the subject; based on the predicted existence of said colorectal or pancreas cancer in the subject; or based on the predicted existence of the carcinoma in the subject.

Thus, the cancer status/disease status as determined or predicted based on the at least two platelet-derived biomarkers according to the embodiments can be used to identify a suitable treatment regimen for a subject.

For instance, the cancer status/disease status predicted for a subject is either cancer or not cancer (malignant or benign). If the predicted cancer status for a subject is cancer, an anti-cancer treatment regimen is selected for the subject. Non-limiting examples of such anti-cancer treatment regimens include chemotherapy, surgery and/or irradiation. If the cancer status/disease status predicted for the subject indicates no cancer, generally no cancer treatment regimen is needed.

In this embodiment selecting the treatment regimen comprises selecting an anti-cancer treatment regimen or no anti-cancer treatment regimen based on the cancer status/disease status.

In another example the cancer status predicted for the subject is either early cancer or advanced. In such a case, the anti-cancer treatment regimen can be selected to be most efficient for the particular cancer status, i.e. early or advanced. For instance, surgery could be a suitable treatment regimen for early cancer optionally complemented with mild drug therapy, such as hormone therapy. A suitable treatment regimen for advanced cancer is typically a systemic therapy, such as chemotherapy and/or irradiation, optionally complemented with surgery and adjuvant therapy.

In this embodiment selecting the treatment regimen comprises selecting a treatment regimen for either early cancer or advanced cancer based on the cancer status.

In a further example the cancer status/disease status predicted for the subject is either benign lesion or malignant tumor. In such a case, the anti-cancer treatment regimen can be selected to be most efficient for the particular cancer status/disease status, i.e. benign or malignant. For instance, surgery or indeed no treatment at all could be a suitable treatment regimen for benign lesion. A suitable treatment regimen for malignant tumor is typically a systemic therapy, such as chemotherapy and/or irradiation, optionally complemented with surgery and adjuvant therapy.

In this embodiment selecting the treatment regimen comprises selecting a treatment regimen for either benign lesion or malignant tumor based on the cancer status/disease status.

Further aspects of the embodiment relates to methods of treating a subject suffering from cancer. In an embodiment, the method comprises measuring a respective amount of each platelet-derived biomarker selected from a group consisting of ITGA2B, WDR1, ACTN1, FLNA, FERMT3, TUBB1 and VCL, or any other biomarker panel defined above, in a biological sample from the subject. Please note that FERMT3 is also denoted FERM herein. The method also comprises calculating a status value based on the amounts. The method further comprises treating the subject with an anti-cancer treatment regimen if the status value exceeds a defined cut off value.

In a particular embodiment according to study 1A, calculating the status value comprises calculating the status value according to equation (1) above. Treating the subject then preferably comprises treating the subject with an anti-cancer treatment regimen if the status value exceeds a cut off value within a range of 0.25 and 0.30, preferably 0.29.

In another embodiment according to study 1A, the method of treating a subject suffering from cancer comprises measuring a respective amount of at least two, preferably each, platelet-derived biomarker selected from a group consisting of ITGA2B, WDR1, ACTN1, FLNA, FERMT3, TUBB1 and VCL, or any other of the biomarker panels defined above, in a biological sample from the subject. The method also comprises comparing the respective amount of the at least two, preferably each, platelet-derived biomarker with a respective reference amount. The method further comprises treating the subject with an anti-cancer treatment regimen if at least one of the respective amount of FERMT3, TUBB1, VCL and basic ITGA2B exceeds the respective reference amount for FERMT3, TUBB1, VCL and basic ITGA2B and/or at least one of the respective amount of WDR1, FLNA, ACTN1 and acidic ITGA2B is below the respective reference amount for WDR1, FLNA, ACTN1 and acidic ITGA2B.

In a particular embodiment according to study 1A, treating the subject comprises treating the subject with an anti-cancer treatment regimen if the respective amount of FERMT3, TUBB1, VCL and basic ITGA2B exceeds the respective reference amount for FERMT3, TUBB1, VCL and basic ITGA2B and if the respective amount of WDR1, FLNA, ACTN1 and acidic ITGA2B is below the respective reference amount for WDR1, FLNA, ACTN1 and acidic ITGA2B.

The respective reference amounts can be determined from a control group or previously from the subject itself as previously discussed herein.

A further aspect of the embodiments relates to a kit comprising a solid support configured to support at least two platelet-derived biomarkers selected from any of the above presented groups. The kit also comprises instructions for using the solid support to measure the at least two platelet-derived biomarkers obtained from a biological sample from a subject. The kit further comprises instructions for determining whether a subject is suffering from a benign lesion or from a carcinoma lesion; for predicting existence of a benign and/or carcinoma lesion in a subject; for predicting existence of colorectal or pancreas cancer in a subject; or for predicting existence of carcinoma in a subject depending on which particular group of platelet-derived biomarkers that is used.

In a particular embodiment the solid support of the kit is a 2-DE gel. The instructions for using the solid support preferably comprise instructions for running 2D gel electrophoresis to separate platelet proteins from the biological sample based on isoelectric point and mass.

The instructions for using the solid support preferably comprise instructions for using the solid support to measure a respective amount of each platelet-derived biomarker in the group from the biological sample.

In an embodiment the instructions for predicting cancer status/disease status could comprise instructions for calculating a status value based on equation (1) above. The instructions for predicting cancer status/disease status preferably also comprises instructions for predicting the cancer status/disease status based on a comparison of the status value and a defined cut off value. The defined cut off value is preferably within a range of 0.25 and 0.30, more preferably equal to 0.29.

The above-described kit can be adapted to be used according to any of the method aspects discussed in the foregoing. In such a case, the instructions for predicting cancer status/disease status are typically replaced by instructions for, based on the measurements, detecting or predicting the occurrence of benign or malignant lesions/tumors in the subject, instructions for correlating the measurement with cancer status/disease status in the subject, instructions for diagnosing a subject based on the measurement, instructions for detecting the presence of cancer in a subject based on the measurement, instructions for determining whether a subject's cancer is early or advanced based on the measurement or instructions for determining whether a subject's lesion/tumor is benign or malignant based on the measurement. Alternatively, the kit could, in addition to the instructions for predicting cancer status/disease status also comprise instructions for selecting treatment regimen for the subject based on the cancer status/disease status.

A related aspect of the embodiments defines a kit comprising a solid support configured to support platelet-derived biomarkers selected from a group consisting of ACTB, ACTN1, ACTN4, AP4A, CASP3, CAZA1, CFL1, CLU, CNDP2, CRKL, ERP29, FERM, FIBG, FLNA, FPPS, GELS, GPIX, GRP75, GSTO1, HDHD2, HP protein, HSP70, HSP71, HSP90AB1, ILEU, ITGA2B, ITB3, ITGA6, KAP3, MLEC, PHB, RINI, SHLB1, SNCA, SPB6, SRC, TBA, TBA4A, THTM, TLN1, TMP1, TSG, TUBB1, VCL and WDR1.

The kit also comprises instructions for using the solid support to measure a respective amount of each platelet-derived biomarker in the group in a biological sample from the subject. The kit also comprises instructions for calculating a status value based on the amounts and instructions for treating the subject with an anti-cancer treatment regimen if the status value for example exceeds a defined cut off value.

In another embodiment, the kit comprises a solid support configured to support platelet-derived biomarkers selected from a group consisting of ACTB, ACTN1, ACTN4, AP4A, CASP3, CAZA1, CFL1, CLU, CNDP2, CRKL, ERP29, FERM, FIBG, FLNA, FPPS, GELS GPIX, GRP75, GSTO1, HDHD2, HP protein, HSP70, HSP71, HSP90AB1, ILEU, ITGA2B, ITB3, ITGA6, KAP3, MLEC, PHB, RINI, SNCA, SPB6, SRC, SHLB1, TBA, TBA4A, THTM, TLN1, TMP1, TSG, TUBB1, VCL and WDR1 in a biological sample from the subject. The kit also comprises instructions for comparing the respective amount of at least two, preferably each, platelet-derived biomarker with a respective reference amount.

In a particular embodiment the instructions for treating the subject comprise instructions for treating the subject with the anti-cancer treatment regimen if the respective amount of FERMT3, TUBB1, VCL and basic ITGA2B exceeds the respective reference amount for FERMT3, TUBB1, VCL and basic ITGA2B and if the respective amount of WDR1, FLNA, ACTN1 and acidic ITGA2B is below the respective reference amount for WDR1, FLNA, ACTN1 and acidic ITGA2B.

Figure 4:
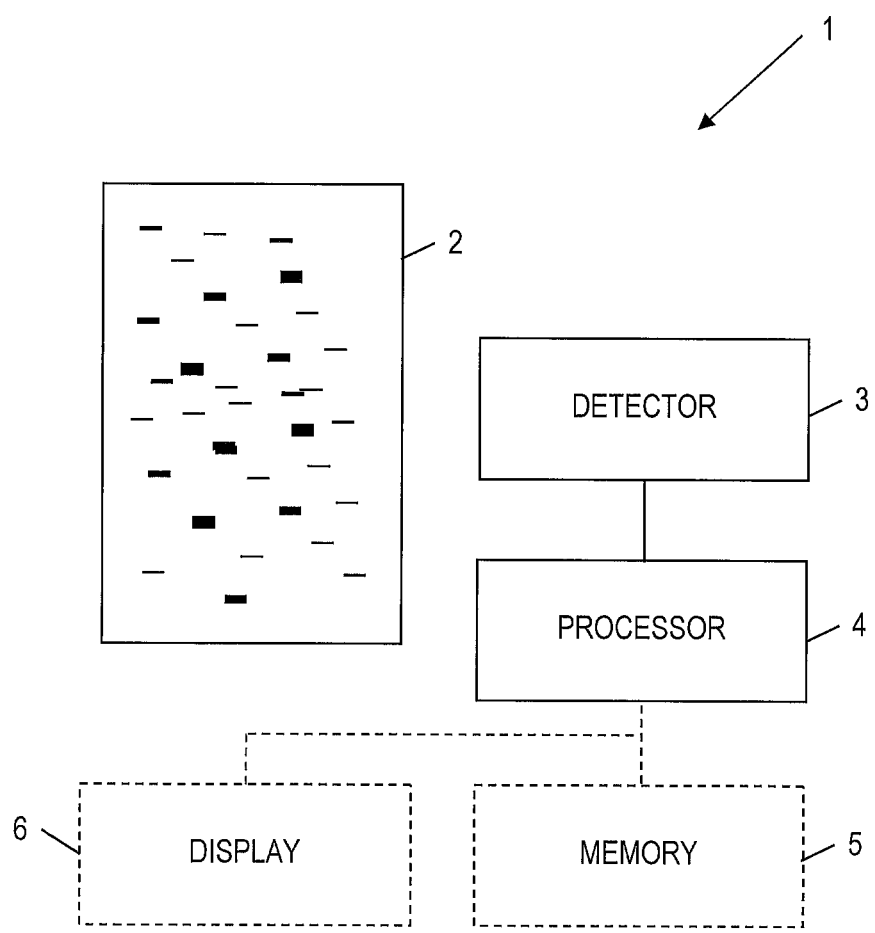
FIG. 4 is a schematic illustration of a diagnostic system according to an embodiment.

A further aspect of the embodiments defines a diagnostic system 1, see FIG. 4. The diagnostic system 1 comprises a solid support 2 configured to support at least two platelet-derived biomarkers selected from a group consisting of ACTB, ACTN1, ACTN4, AP4A, CASP3, CAZA1, CFL1, CLU, CNDP2, CRKL, ERP29, FERM, FIBG, FLNA, FPPS, GELS, GPIX, GRP75, GSTO1, HDHD2, HP protein, HSP70, HSP71, HSP90AB1, ILEU, ITGA2B, ITB3, ITGA6, KAP3, MLEC, PHB, RINI, SHLB1, SNCA, SPB6, SRC, TBA, TBA4A, THTM, TLN1, TMP1, TSG, TUBB1, VCL and WDR1. The diagnostic system 1 also comprises a detector 3 configured to detect, on the solid support 2, the at least two platelet-derived biomarkers from a biological sample from a subject. The detector 3 is also configured to generate a respective estimate of an amount of the at least two platelet-derived biomarkers. The detector 3 is preferably connected to a processor 4 of the diagnostic system 1. The processor 4 is configured to process the respective estimate of the amount. The processor 4 is also configured to generate estimation whether a subject is suffering from a benign lesion or from a carcinoma lesion; a prediction of existence of a benign and/or carcinoma lesion in a subject; a prediction of existence of colorectal or pancreas cancer in a subject; or a prediction of existence of carcinoma in a subject depending on which particular group of platelet-derived biomarkers that is used.

In a particular embodiment the solid support 2 is a 2-DE gel 2 configured to separate platelet proteins from the biological sample based on isolectric point (isoelectric focusing) and mass (SDS-PAGE).

In a particular embodiment the detector 3 is configured to detect, on the solid support 2, each platelet-derived biomarker in the group from the biological sample and generate a respective estimate of an amount of each platelet-derived biomarker.

The detector 3 could be any detector configured to take an image of the solid support 2. A non-limiting example of a detector 3 that can be used according to the embodiments is an Epson Image Scanner with 16 bits resolution. Any high-resolution image scanner, appropriate for the purpose may be applicable for use in the current invention.

The reference amounts can be stored in a memory 5 connected to the processor 4. These reference amounts can previously have been determined for the particular subject and then entered in the memory 5. Alternative, the reference amounts can previously have been determined for a control group using the diagnostic system 1. A further alternative is that the reference amounts have been input to the diagnostic system 1 and the memory 5 by a user using a suitable user input, such as a keyboard (not shown) or a touch-sensitive display 6.

In an alternative embodiment the processor 4 is configured to calculate a status value according to equation (1) above based on the respective amounts of the platelet-derived biomarkers. The above-mentioned memory 5 is then preferably configured to store a defined cut off value. The processor 4 is then configured to compare the status value with the defined cut off value and generate the prediction of cancer status in the subject based on the comparison.

The predicted cancer status/disease status is preferably displayed to a user on a display 6 of or connected to the diagnostic system 1. The displayed cancer status/disease status could be cancer versus no cancer, early cancer versus advanced cancer or benign tumor versus malignant tumor.

The processor 4 can be any computer or processing terminal having hardware and/or software means configured to perform the processor operations disclosed in the foregoing. A non-limiting example of a processor 4 includes a computer comprising the software SameSpots.

A further aspect of the embodiments relates to a computer program product configured to predict cancer status/disease status in a subject. The computer program product comprises a computer readable media having computer readable program code embodied therein. The computer readable program code comprises computer readable program code configured to measure at least two platelet-derived biomarkers according to the embodiment in a biological sample from the subject. The computer readable program code also comprises computer readable program code configured to generate estimation whether a subject is suffering from a benign lesion or from a carcinoma lesion; a prediction of existence of a benign and/or carcinoma lesion in a subject; a prediction of existence of colorectal or pancreas cancer in a subject; or a prediction of existence of carcinoma in a subject depending on which particular group of platelet-derived biomarkers that is used.

Diagnosing or diagnosis as used herein means providing an indication that a subject may be afflicted with a disease, e.g. cancer, such as ovarian cancer, prostate cancer, colorectal cancer or pancreatic cancer. It will be appreciated that no such technique is perfect and that such diagnosis may be confirmed by other procedures such as physical examination, imaging, histological examination of tissue samples, etc.

A break-through regarding personalized cancer treatment would be a blood test making it possible to distinguish between (1) completely healthy or some cell/tissue alterations (benign or malignant lesions present) and/or (2) non-cancer (benign) and cancer (malign), and/or (2) early (often local) and advanced (often disseminated or metastatic) tumor disease. The test should have the possibility to distinguish between normal healthy individuals and individuals with altered cells/tissue (such as lesions/tumors), i.e. to discriminate between healthy subjects and subjects with some kind of cell or tissue alteration such as benign or malign lesions. The test should further be able to determine whether subjects with altered cells/tissue (lesions/tumors) have benign lesions or malign tumors (cancer), i.e. to discriminate between benign lesions and malign tumors. The test should also be able to determine/distinguish whether subjects with malign neoplastic disease (cancer, malign tumors) are in an early or advanced stage of the disease, i.e. to discriminate between early and advanced cancer.

The disclosed methods of detecting cancer for a diagnosis or development of a treatment regime may also be used in combination with other diagnostic methods, including, but not limited to, performing a biopsy, performing a scan (X-ray, MRI, PET, CT, and the like), and screening for other biomarkers or other indicators of the possibility of disease. Those skilled in the art will appreciate that this listing of other methods of detecting disease for a diagnosis or screening is by no means exhaustive, and is but a small sampling of the other possible diagnostic methods that can easily be combined with the disclosed methods for purposes of diagnosis for cancer such as ovarian cancer, prostate cancer, colorectal cancer and/or pancreatic cancer.

Subjects as described herein include human subjects and patients as well as other mammals in veterinarian or research settings, including mice. The subjects may be male or female and may be of any race or ethnicity, including but not limited to Caucasian, African-American, African, Asian, Hispanic, Indian, etc. The subjects may be of any age, including newborn, neonate, infant, child, adolescent, adult, and geriatric. Subjects may also include animal subjects, particularly mammalian subjects such as dog, cat, horse, mouse, rat, etc., screened for veterinary medicine or pharmaceutical drug development purposes. Subjects include but are not limited to those who may have, possess, have been exposed to, or have been previously diagnosed as afflicted with one or more risk factors for cancer. Risk factors include age, gender, race, smoking, diet, obesity, diabetes, work exposure, family history, alcohol and drug use and the like. These risk factors may be considered in combination with the disclosed methods of detecting cancer for a diagnosis or screening.

Several experimental studies have been performed by the inventors, which have revealed platelet-derived biomarker panels useful for cancer prediction and diagnosis. Study 1 revealed markers for ovarian cancer. Study 1A revealed 7 markers useful for determining cancer status and progression, Study 1B revealed 21 markers, an additional 16 markers (5 overlapping) giving a total of 23 markers, useful for predicting or diagnosing ovarian cancer, and Study 1C revealed 10 markers useful for discriminating between healthy subjects and subjects with some kind of lesion (benign or malignant lesions). Study 2 regarding prostate cancer indicated that the 23 markers from Study 1 also applies for prostate cancer. Study 3 and 4 identified 23 markers for pancreatic and/or colorectal cancer, wherein 22 where applicable for both cancers, and one was pancreatic cancer specific and one colorectal cancer specific. A panel of 12 markers where shown to be identical in all cancers, thus able to use for diagnosis regardless of which cancer being diagnosed. In total, all studies revealed 45 unique biomarkers useful for diagnosing and predicting cancer and cancer status. Some markers where shown to be up-regulated, and some down regulated. However, depending on the method used for evaluating the biomarkers, this might change. Therefore, it is a general concept of the present invention that an alteration of the relative amount of the biomarker profile (for a given panel) above a certain threshold, as defined in more detail below, regardless if it is an increase or decrease, is considered as equally interesting when predicting/diagnosing cancer and/or cancer status and/or the occurrence of lesions (altered tissue) as described in the present invention Study 1A Experimental data from study 1A, as further presented herein, has indicated that the seven platelet-derived biomarkers disclosed therein, in one of the embodiments, may be divided into two groups with regard to the change or alteration in the amount of the biomarker expressed by or at least present in platelets from subjects having cancer vs. non-cancer patients (benign) and allowing diagnosis of subjects with early cancer.

It is important to note that the markers may increase or decrease depending on the detection and analysis method used. Nonetheless, a first group of the platelet-derived biomarkers in study 1A showed an increase in the relative amount of the biomarker for a severe cancer status. Thus, subjects having cancer or subjects having advanced cancer or early cancer generally have higher altered (higher) relative amounts of these biomarkers as compared to subjects with no cancer or subjects having benign lesions. This first group consists of FERMT3, TUBB1, VCL and basic ITGA2B. Basic ITGA2B indicates ITGA2B isoforms that are found on a basic portion of a two-dimensional electrophoresis gel, i.e. have an isoelectric point at a pH above 6 and are therefore negatively charged at neutral pH.

A second group of the platelet-derived biomarkers in study 1A showed a decrease in the relative amount of the biomarker for a severe cancer status. Thus, subjects having cancer or subjects having advanced cancer generally have lower relative amounts of these biomarkers as compared to subjects with no cancer or subjects having benign lesions. This second group consists of WDR1, FLNA, ACTN1 and acidic ITGA2B. Acidic ITGA2B indicates ITGA2B isoforms that are found on an acidic portion of a two-dimensional electrophoresis gel, i.e. have an isoelectric point at a pH below 6 and are therefore positively charged at neutral pH.

In an embodiment the at least two platelet-derived biomarkers are selected from the first group mentioned above. In such a case, predicting the cancer status in the subject can be based on whether the amount of the at least two platelet-derived biomarker have increased, preferably increased above a reference amount.

In another embodiment the at least two platelet-derived biomarkers are selected from the second group. In such a case, predicting the cancer status in the subject can be based on whether the amount of the at least two platelet-derived biomarker have decreased, preferable decreased below a reference amount.

The respective reference amount to which the respective amount of the at least two platelet-derived biomarkers is compared (individually) to can be a reference amount determined for the relevant platelet-derived biomarkers in a control group. For instance, if the prediction is either altered tissue present or no altered tissue (lesions) present, the control group can be a group of healthy subjects having no detectable altered tissue (lesions). The amount of the at least two platelet-derived biomarkers is then measured for the control group and the reference amount is determined from this control group, such as an average or median of the amounts determined for the healthy subjects in the control group. For ovarian and prostate cancer discriminating healthy subjects from subjects with lesions, the at least two biomarkers measured/detected should be chosen from the specific biomarker platelet consisting of AP4A, CAZA1, CNDP2, GPIX, ILEU, KAP3, PHB, SHLB1, SPB6 and TMP1.

Likewise, when altered tissue (lesions) is present in the subject and the prediction is of cancer status, either cancer present or no cancer present (benign), the control group can be a group of benign controls, i.e. subjects diagnosed as having only benign lesions present. Similarly, the amounts of the at least two platelet-derived biomarkers are then measured for the control group and the reference amount is determined from this control group, such as an average or median of the amounts determined for the healthy subjects in the control group. This procedure can also be applied to the case when the cancer status is advanced cancer or tumor versus early cancer or tumor. The control group can then advantageously be subjects having diagnosed early cancer.

In an alternative approach, the reference amount can be determined from the subject itself prior to disease development, i.e. prior to any cancer or during a period when the subject only had early cancer or benign lesion(s).

An amount of a biomarker in a biological sample may be the quantity or concentration of the biomarker in the biological sample, a score based on the detected amounts of the biomarker in the biological sample, a percentile based on a population of patients, a quantitative amount or semi-quantitative amount of the biomarker in the biological sample, or other suitable quantities based on the detected biomarker.

Increase or decrease in the amount of a platelet-derived biomarker as used herein refers to an increased relative amount or a decreased relative amount in the relative amount of the platelet protein detectable in or via a biological sample removed or derived from a subject as compared to a relative reference amount of the platelet protein in a control. A control sample includes a biological sample from a corresponding subject not afflicted with a cancer (e.g. ovarian cancer, prostate cancer) or a biological sample from a non-diseased tissue or non-diseased portion of a tissue from the same subject or a biological sample from the same subject prior to disease development. A presence or absence of a detectable amount of a platelet-derived biomarker may also be considered an increase or decrease.

Increase or decrease in the amount of a platelet-derived biomarker as used herein could for example refer to an increased amount (e.g. a 10%, 20%, 30%, 40%, 50%, 100% increase, or more) or a decreased amount (e.g. a 10%, 20%, 30%, 40%, 50%, 100% decrease, or more) in the amount of the platelet protein detectable in or via a biological sample removed or derived from a subject as compared to a reference amount of the platelet protein in a control.

Regarding ovarian cancer, an international system of staging of ovarian cancer identifies the spread at the point of diagnosis. The correct staging as the moment of primary diagnosis impacts the treatment decisions. The staging system is called the FIGO system, after its authors—the International Federation of Gynaecological Oncologists. According to the 2013 FIGO staging system for ovarian cancer, stage 1 is characterized by the tumor confined to the ovary/ovaries or fallopian tube(s), stage 2—the tumour involves one or both ovaries or fallopian tubes with pelvic extension (below pelvic brim) or primary peritoneal cancer, stage 3—the tumour involves one or both ovaries or fallopian tubes, or primary peritoneal cancer, with confirmed (cytologically or histologically) spread to the peritoneal surfaces involving both pelvic and abdominal peritoneum and/or metastasis to the retroperitoneal lymph nodes, and stage 4—distant metastasis beyond the peritoneal cavity (including parenchymal liver/splenic metastases and extra-abdominal metastases.

In a further embodiment the method comprises measuring, in the biological sample, a respective amount of at least one platelet-derived biomarker from the first group from study 1A and measuring, in the biological sample, a respective amount of at least one platelet-derived biomarker from the second group. Hence, in this embodiment at least one of the measured platelet-derived biomarkers is expected to increase for a severe cancer status whereas at least another of the measured platelet-derived biomarkers is expected to decrease for a severe cancer status.

In such a case, a status value can be calculated for the subject based on the at least two determined amounts, preferably as a quotient between the two determined amounts. Such a quotient could be between the amount of the platelet-derived biomarker from the first group divided by the amount of the platelet-derived biomarker from the second group. Such a quotient will then be significantly higher for a subject suffering from cancer as compared to a subject with no cancer, be significant higher for a subject with spread cancer as compared to a subject with local cancer and be significant higher for a subject with a malignant tumor as compared to a subject with a benign tumor. An alternative is to calculate a quotient between the amount of the platelet-derived biomarker from the second group divided by the amount of the platelet-derived biomarker from the first group. In such a case, the quotient will be significant lower for a subject suffering from cancer as compared to a subject with no cancer, be significant lower for a subject with spread cancer as compared to a subject with local cancer and be significant lower for a subject with a malignant tumor as compared to a subject with a benign tumor.

If more than one platelet-derived biomarker is measured from the first group and/or for the second group the sums of the amounts of the platelet-derived biomarkers from the first group is preferably divided by the sum of the amounts of the platelet-derived biomarkers from the second group, or vice versa.

The methodology of the invention can, besides being used as an assay for the diagnosis of the various cancers that are indicated, also be used in combinations. If run on a multiplex platform (i.e. Luminex or other) all biomarkers for the indications and the common group are run in one analysis. From that assay the various different diagnosis results can be filtered out separately. Combinations of assays can be designed so that any combination of Ovarian, Prostate, Pancreatic, Colorectal and the common group can be combined together in a pair on in larger groups. This will enable the analysis of cancer or not in combination with a specific cancer.

Embodiments from Study 1A

In a particular embodiment a respective amount of each platelet-derived biomarker of the embodiments, i.e. ITGA2B, WDR1, ACTN1, FLNA, FERMT3, TUBB1 and VCL, is preferably measured in the biological sample.

In such a case, the prediction of the cancer status in the subject can be based on any increase in the respective amounts of FERMT3, TUBB1, VCL and basic ITGA2B and any decrease in the respective amount of WDR1, FLNA, ACTN1 and acidic ITGA2B preferably relative to a respective reference amount.

In a particular embodiment a status value is calculated based on the measured amounts of the platelet-derived biomarkers of the embodiments. In an embodiment the status value is calculated based on a first sum of the respective amount of the platelet-derived biomarkers from the first group, i.e. FERMT3, TUBB1, VCL and basic ITGA2B, and based on a second sum of the respective amount the platelet-derived biomarkers from the second group, i.e. WDR1, FLNA, ACTN1 and acidic ITGA2B. In an embodiment the status value is calculated based on a quotient between the first sum and the second sum. Hence, in a particular embodiment the status value is calculated as:

$$([FERMT3]+[TUBB1]+[VCL]+[ITGA2B]_{basic})/([WDR1]+[FLNA]+[ACTN1]+[ITGA2B]_{acidic}) \qquad (1)$$

wherein $[ITGA2B]_{basic}$ represents an amount of negatively charged ITGA2B, $[ITGA2B]_{acidic}$ represents an amount of positively charged ITGA2B and [X] represents an amount of the relevant platelet-derived biomarker, with X=FERMT3, TUBB1, VCL, WDR1, FLNA or ACTN1.

In the above disclosed embodiments where a status value is calculated based on the amounts of the measured platelet-derived biomarkers, this status value is preferably compared to a defined cut off value. Hence, in such embodiments the prediction of the cancer status preferably comprises comparing the status value with a defined cut off value and predicting the cancer status in the subject based on the comparison, i.e. whether the status value is above or below the cut off value.

The algorithm defined in equation (1) produces low values for non-cancerous or benign biological samples, intermediate values for local cancer and high values for malignant or disseminated/advanced cancer.

The cut off value can be determined by calculating the status value for a group of cancer subjects and for a control group of healthy subject, for a group of subjects with spread cancer and for a control group with early cancer or for a group of subjects with malignat tumors and for a control group of subjects with benign lesions. In such a case, the cut off value could be defined based on a comparison of the status values from the two groups. In a particular embodiment, the cut off value is calculated as:

$$[(\text{mean value Cancer}-1\ SDEV)+(\text{mean value Controls}+1\ SDEV)]\times\tfrac{1}{2} \qquad (2)$$

wherein mean value Cancer represents the mean status value obtained from the group of cancer subjects, for the group of subjects with advanced cancer or for the group of subjects with malignant tumors, SDEV represents standard deviation and mean value Controls represents the mean status value obtained from the control group.

A suitable value of the cut off value typically depends on the particular cancer type and typically based on the cancer status, i.e. cancer versus non-cancer, advanced cancer versus early cancer or malignant tumor versus benign lesion. The cut off value can be determined as specified above using equations (1) and (2) for the relevant cancer type and cancer status.

In an embodiment, the cut off value is advantageously within a range of 0.25 and 0.30 and preferably equal to 0.29. This cut off value has been determined, as further disclosed herein, for a group of subjects suffering from malignant ovarian cancer and a control group with benign lesions, e.g. myoma in the uterus or benign cystic adenoma.

In a particular embodiment a cut off value within the range of 0.25 and 0.30, preferably equal to 0.29, is used for discriminating between cancer and no cancer. A subject not suffering from any cancer typically has a status value as calculated using equation (1) within the range of 0.05 and 0.25. Correspondingly, a subject suffering from cancer typically has a status value as calculated using equation (1) within the range of 0.30 and 0.60.

A suitable cut off value for discriminating between advanced cancer and early cancer will, at least for ovarian cancer, typically be within the range of 0.25 and 0.60, such as within the range of 0.30 to 0.60. Correspondingly, a suitable cut off value for discriminating between malignant tumors and benign tumor could typically be within the range of 0.25 to 0.60, such as within the range of 0.30 and 0.60.

Study 1B

Following Study 1A and the general positive outcome of that a wider study was initiated to further validate the biomarkers. In this study a larger cohort of patients was used in order to have enough patients to cover the normal biological variability as well as the biological spread of the cancer itself. A more advanced evaluation strategy involving PLS based statistical analysis of the results was also used. Study 1B included sixteen benign controls (BC) and twenty women with defined advanced ovarian cancer spread to the abdomen (SC). The controls were women with benign lesions, e.g. myoma in the uterus or benign cystic adenoma. All patients were diagnosed and treated at the Department of Obstetrics and Gynaecology, Karolinska University Hospital-Solna. Patients donated blood for the study in accordance with the permission of Local Ethical Committee Dnr. 2010/504-31. Platelets were prepared and analyzed according to standardized procedures described (example 1 and 2). After image analysis of 2D-gel separated proteins, data representing all samples were further analyzed by multivariate statistics (partial least square discriminant analysis, PLS). A PLS model with two components showed the best results (see FIG. 5). A sensitivity of 90% and a specificity of 94% was obtained for the optimized and cross validated model. Variables were ranked according to their contribution to the prediction using the VIP (variable of importance) parameter. Top-ranked variables (protein spots representing highest VIP value) were then selected for identification by mass spectrometry. In total >75% of the top-16 ranked proteins, and >50% of the top-50 ranked proteins were identified. Successful identifications are listed in table 4, some identifications were excluded since they were regarded as less feasible for validation. The following biomarker candidates were selected, sorted according to VIP-rank (given within brackets [VIP-rank]): ERP29 [1], ACTN4 [3], HP [4, 8], TLN1 [6, 10, 11, 12, 27, 50], SRC [6], ITB3 [13], HSP71 [16], TBA4A [19], ITA2B [24], TBA [25], CRKL [26], GRP75 [32], GELS [34, 79], TUBB1 [37], HSP70 [39], FIBG [40], and ITA2B [45]. One additional biomarker candidate (RINI) was found by ANOVA analysis of the data set ($p<0.05$). For details, see Tab 4 and Tab (summary).

To evaluate the model, an independent test set of eleven SC and eight LC samples was used. A prediction model was built using the training set including the model parameters selected from the model optimization procedure. Results showed that nine of eleven SC samples and all eight LC samples were correctly classified, which correspond to an 89% sensitivity for the classification model.

Thus, we believe that we for the first time have shown new platelet-derived biomarker panels, which might be used for non-invasive diagnosis or prediction of cancer status in a subject suffering from highly malignant cancers, such as ovarian, colorectal or pancreatic cancer, or prostate cancer. Today microscopic examination by a pathologist is needed in order to determine the cancer status, which may result in varying results dependent on the pathologist. The present embodiments provide for a more objective diagnosis and prognosis of cancer than what is used today. The present embodiments allow for diagnosis, treatment and prognosis of cancer without the need for biopsies. The combination of platelet-derived biomarkers is designed for the separation between healthy controls, (no cancer, no lesions), benign controls (no cancer, benign lesions) and cancer samples as well as for separation of early, often local, non-disseminated cancer, and advanced cancer from these two groups, which in turn would have significant impact on the choice of treatment strategy.

EXAMPLES

Example 1—Study 1A

Patients and Sample Preparation

The study included eleven controls and six women with defined ovarian cancer spread to the abdomen. The controls were at the age between 42-70 years (mean age 65 year). The controls were women with benign lesions, e.g. myoma in the uterus or benign cystic adenoma. The cancer patients were between 49-74 years (mean age 67 year). All patients were diagnosed and treated at the Department of Obstetrics and Gynaecology, Karolinska University Hospital-Solna, Sweden. See Table 1 below.

TABLE 1

Control and cancer patients

| Patient Sample | Diagnosis | Age |
| --- | --- | --- |
| KTR19 | Control patient. Serous cystadenoma, benign. | 73 |
| KTR25 | Control patient. Serous cystadenoma, benign. | 72 |
| KTR29 | Control patient. Cystadenofibroma and cystadenoma, benign. | 63 |
| KTR34 | Control patient. Myoma, benign. | 67 |
| KTR40T | Control patient. Mucinous cystadenoma, benign. | 41 |
| KTR45T | Control patient. Myoma, benign. | 79 |
| KTR57a + b | Control patient. Cystic lesion, benign. | 67 |
| KTR67 | Control patient. Myoma, benign. | 81 |
| KTR68 | Control patient. Serous cystadenoma, benign. | 45 |
| KTR79 | Control patient. Cystic endometriosis, benign. | 48 |
| STR95 | Ovarian cancer. Disseminated, malignant. | 65 |
| STR82 | Ovarian cancer. Disseminated, malignant. | 49 |
| STR85 | Ovarian cancer. Disseminated, malignant. | 74 |
| STR87a + b | Ovarian cancer. Clinically advanced, malignant. | 73 |
| STR89 | Ovarian cancer. Clinically advanced, malignant. | 70 |

Isolation Method (the Same Method is Used in Study 1B and 1C)

Isolation of platelets was performed by three centrifugation steps. The blood was obtained in vaccutainer tubes containing ethylenediaminetetraacetic acid (EDTA) to prevent coagulation, processed within 30 minutes and kept at room temperature. The patient information was collected and each sample was given a unique identification code.

The first centrifugation was performed at 1500 g, 10 minutes at +4° C. The plasma was collected and the erythrocytes were discarded. The collected plasma was then centrifuged 3700 g, 10 minutes at +4° C. The platelet poor plasma (PPP), was collected in Eppendorf tubes 5×1 mL and stored at −70° C. for further analysis. The remaining pellet (the isolated platelet fraction) was resuspended and washed in 500 µL 0.9% NaCl, centrifuged in an Eppendorf centrifuge, 5600 g, 10 minutes, +6° C. The supernatant was discarded and the weight of the pellet was recorded. Representative samples of the platelet pellet were prepared and the quality and purity of the platelet isolation was confirmed by microscopy.

The platelet fraction were extracted and further lyophilized to complete dryness and resuspended in lysis buffer containing 9 M urea, 2 M thiourea, 1 M EDTA, 25 mM 3-8(3-cholamidopropyl) dimethylammonio]-1-propanesulfonate (CHAPS), protease inhibitors and carrier ampholytes.

The platelet protein lysate were shaken 3 hours at room temperature followed by 15 minutes centrifugation at 12000 RPM. The supernatant were collected and the protein concentration was measured using the Bradford protein analysis protocol (Quick Start™ from Bio-Rad Laboratories).

Protein Separation

Prior to two-dimensional gel electrophoresis (2-DE) analysis, the protein lysate was diluted to a concentration of 75.0 µg total protein in 300 µL rehydration buffer containing 7 M urea, 2 M thiourea, 65 mM CHAPS, 0.5% Triton X100, 0.5% v/v mmobilized pH gradient (IPG) buffer pH 4-7 and 18 mM dithiotreitol for each sample.

The first separation step was isoelectric focusing (IEF) where the proteins are separated regarding to their isoelectric point and is run for 22.5 hours. 17 cm long, pH 4-7 IPG strips (BioRad) were used.

The second dimension, sodium dodecyl sulfate polyacrylamide gel electrophoresis (SDS-PAGE), separate the proteins regarding their molecular weight. The 2-DE gel was a 10-13% acrylamide gradient with piperazine diacrylamide (FDA) as cross linker, with a size of 200×250×1.5 mm. Sample proteins were separated for approximately 20 hours at 100 volt, 12° C.

The SDS gels were silver stained using a mass spectrometry compatible staining protocol and scanned in an Epson Image Scanner III, 16 bits resolution. The images were further analyzed using the software Progenesis SameSpots (Nonlinear Dynamics Limited).

Identification of Proteins by Mass Spectrometry Analysis

Silver-stained bands were excised from the gels, treated for in-gel digestion and analyzed at the Ludwig Institute, Uppsala, essentially as described previously (Hellman, U. (2000) Sample preparation by SDS/PAGE and in-gel digestion. EXS 88, 43-54.). Briefly, the silver was destained using Farmer's reagent, and trypsin (porcine, modified, sequence grade, Promega, Madison, Wis.) was introduced to the dried gel pieces. After overnight tryptic digestion, the peptides were bound to a C18 ZipTip column, washed, and then eluted with acetonitrile containing the matrix (alfa-cyano 4-hydroxy cinnamic acid) directly onto the target plate. The mass lists were generated by MALDI-TOF mass spectrometry on an Ultraflex III TOF/TOF from Bruker Daltonics, Bremen, Germany. The search for identity was performed using the search engine MASCOT (Matrix Science, London, England) by scanning the current version of NCBI nr sequence database. The spectrum was internally calibrated using autolytic tryptic peptides, and the tolerance was set at 0.02 Da, Oxidation of methionine was allowed. The significance of the identity was judged from the search engine's scoring system.

Results and Discussion

Figure 1:
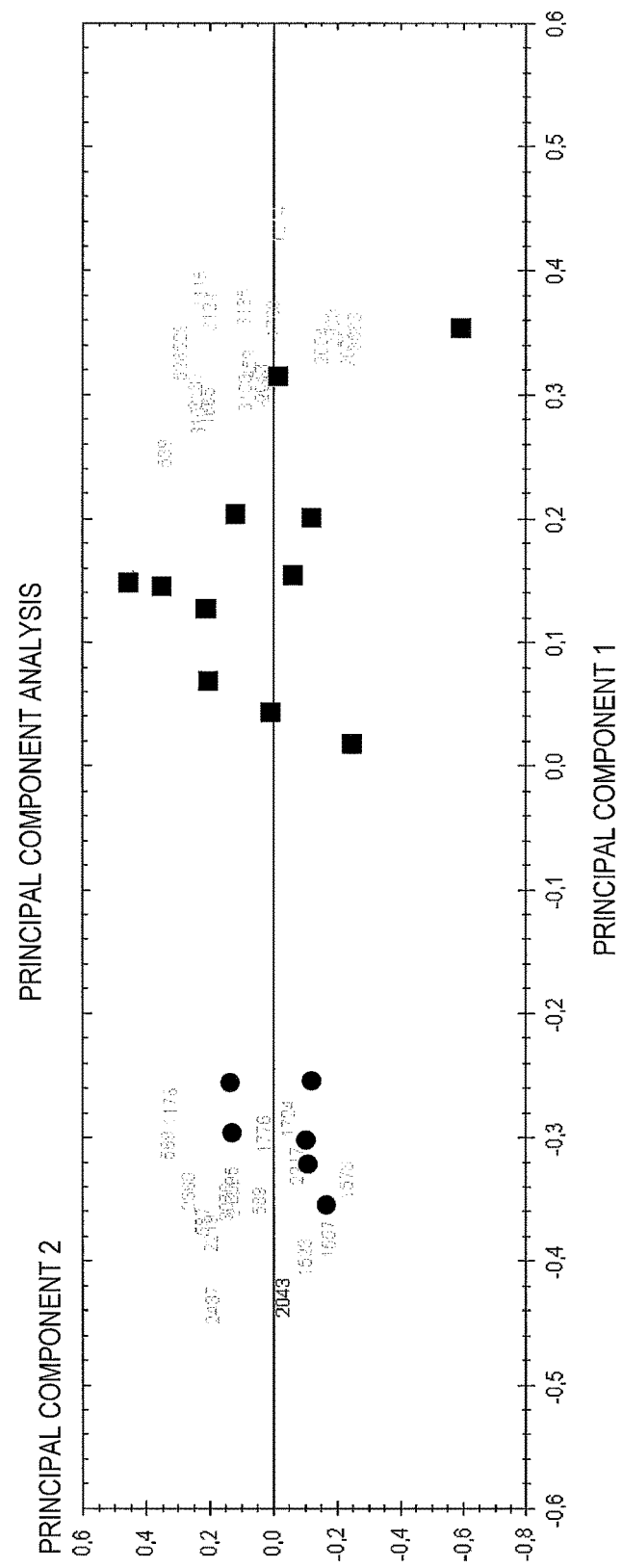
FIG. 1 shows principal component analysis (PCA) from study 1A of samples representing spread cancer versus controls. Black dots represent spread cancer samples and the black squares represent the controls.

Thirty-five increased or decreased protein spots were found when comparing controls and patients with spread ovarian cancer (FIG. 1). In total 19 spots were decreased and 17 spots were increased in spread ovarian cancer.

Identification of Proteins

All together, 35 protein spots were excised and analyzed by mass spectrometry. We obtained 15 successful identifications; 8 protein spots were decreased in the cancer group and 7 protein spots were increased compared to controls (Table 2).

TABLE 2

Identification of biomarkers

| Protein identity[1] | Acc#[2] | # of spots[3] | |
|---|---|---|---|
| ITGA2B[4] (#569, 587, 589) | EAW51594 pI: 6.4-6.6 P08514 Mr: 105-130 | 3 | ↑ |
| ITGA2B[4] (#459, #526, #529, #539) | EAW51594 pI: 5.0-5.1 P08514 Mr: 104 | 4 | ↓ |
| WDR1 (#1214, 1665) | BAD92983 pI: 6.5 Mr: 68 and pI: 6.6 Mr: 68 | 2 | ↓ |
| FERMT3 (#1724) | NP_113659 pI: 6.3-6.4 Mr: 44-76 | 1 | ↑ |
| ACTN1 (#2030) | AAI27125 pI: 5.3 CAA38970 Mr: 38 | 1 | ↓ |
| TUBB1 (#2360) | NP_110400 pI: 5.8 Mr: 30 | 1 | ↑ |
| VCL (#3078, #3095) | EAW54547: pI: 6.7 Mr: 120 and NP_003364: pI: 6.6 Mr: 120 | 2 | ↑ |
| FLNA (#1760) | AAH14654 pI: 6.0 Mr: 43 | 1 | ↓ |

[1]spot number #
[2]observed isoelectric point (pI) and molecular mass (Mr)
[3]arrow show increase or decrease
[4]Integrin alpha 2b is represented by 7 different protein spots, four protein spots were decreased in cancer and the remaining three protein spots were increased.

Figure 2:
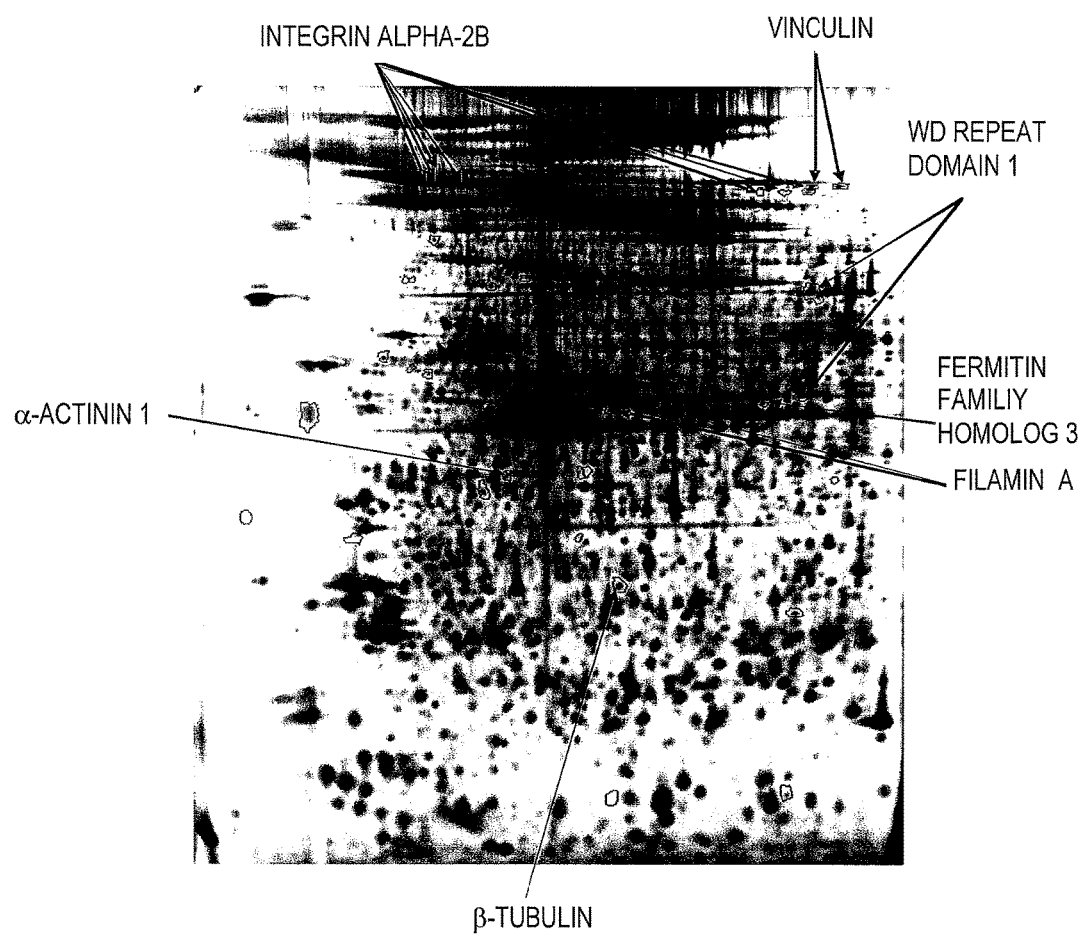
FIG. 2 shows the result from study 1 of a 2D gel separation of platelet proteins on a 2DE gel, where identified spots are marked out. Arrows indicate the location of identified biomarkers.

The Integrin, alpha 2b was represented by 7 out of the 15 protein spots identified. When looking at the position we observed that 4 of them are located at the acidic part of the gel and above 100 kDa and are decreased (FIG. 2). A decreased level of phosphorylated isoforms of Integrin, alpha 2b may have connection with the loss of function in cancer. The other two identified Integrins are located to the right in the 2-DE gels, above 100 kDa and they are increased. The Integrins have at least 13 phophorylation sites that probably give the "train formation" of protein spots and may result in many different post-translational modifications.

Diagnostic Algorithm

The relative quantity of the biomarkers was calculated according to the following diagnostic algorithm:

$$([FERMT3+TUBB1+VCL]+[ITGA2B\ (basic)])/([WDR1+FLNA+ACTN1]+[ITGA2B\ (acidic)]) \quad (3)$$

A cut off value discriminating cancer from non-cancer was defined as:

$$[(mean\ value\ Cancer-1\ SDEV)+(mean\ value\ Controls+1\ SDEV)] \times \tfrac{1}{2} \quad (4)$$

wherein mean value Cancer represents the mean value obtained using the diagnostic algorithm (3) above applied to the six cancer patients, SDEV represents standard deviation and mean value Controls represents the mean value obtained using the diagnostic algorithm (3) above applied to the eleven controls.

Figure 3:
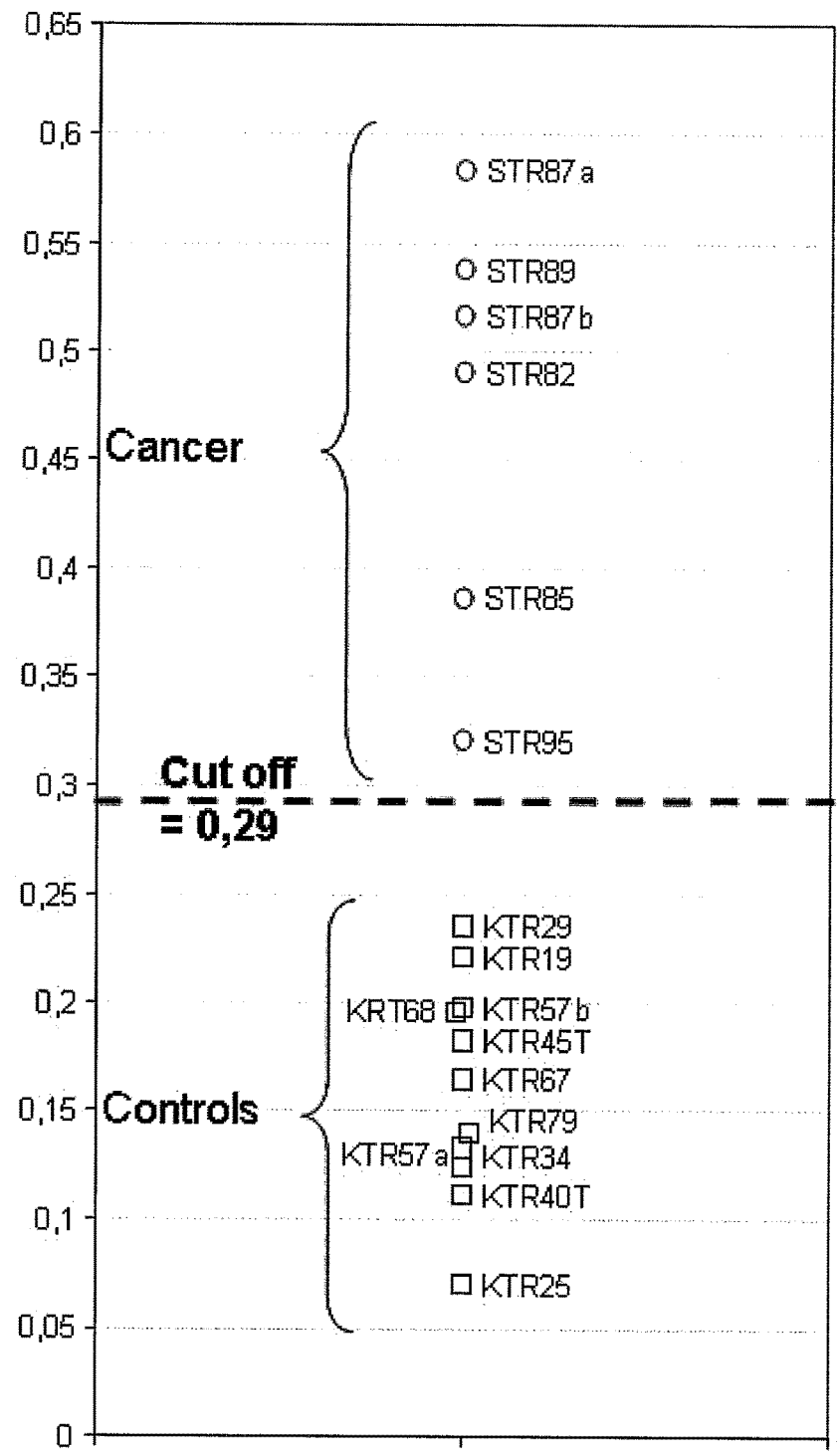
FIG. 3 shows the distribution of samples from study 1A based on a calculation of internal quotes from normalized integrated spot volumes. The algorithm provides clear separation between cancer samples and controls.

FIG. 3 illustrates the output value of the diagnostic algorithm (3) above for the 17 samples. The cut off value obtained from the equation (4) above was 0.29.

Example 2—Study 1B

Study 2 included sixteen benign controls (BC) and twenty women with defined advanced ovarian cancer spread to the abdomen (SC). The controls were women with benign lesions, e.g. myoma in the uterus or benign cystic adenoma. All cancer patients were diagnosed at the Gyneacology Ultrasound department, Karolinska University Hospital. Platelets were prepared and analyzed according to standardized procedures described (example 1 and 2). After image analysis of 2D-gel separated proteins, data representing all samples were further analyzed by multivariate statistics (partial least square discriminant analysis, PLS). A PLS model with two components showed the best results (see FIG. 5). A sensitivity of 90% and a specificity of 94% was obtained for the optimised and cross validated model.

Variables were ranked according to their contribution to the prediction using the VIP (variable of importance) parameter. Top-ranked variables (protein spots representing highest VIP value) were then selected for identification by mass spectrometry. In total >75% of the top-16 ranked proteins, and >50% of the top-50 ranked proteins were identified. Successful identifications are listed in table 4, some identifications were excluded since they were regarded as less feasible for validation. The following biomarker candidates were selected, sorted according to VIP-rank (given within brackets [VIP-rank]): ERP29 [1], ACTN4 [3], HP [4, 8], TLN1 [6, 10, 11, 12, 27, 50], SRC [6], ITB3 [13], HSP71 [16], TBA4A [19], ITA2B (ITGA2B) [24], TBA [25], CRKL [26], GRP75 [32], GELS [34, 79], TUBB1 [37], HSP70 [39], FIBG [40], and ITA2B [45]. One additional biomarker candidate (RINI) was found by ANOVA analysis of the data set (p<0.05). For details, see Tab 4 and Tab (summary). To evaluate the model, an independent test set of eleven SC and eight LC samples was used. A prediction model was built using the training set including the model parameters selected from the model optimization procedure. Results showed that nine of eleven SC samples and all eight LC samples were correctly classified, which correspond to an 89% sensitivity for the classification model.

Patients and Sample Preparation

The study included 16 controls and 31 women with defined ovarian cancer spread to the abdomen. The controls had a mean age of 62±14 (sdev) years and were collected at the Department of Obstetrics and Gyneacology, Karolinska University Hospital-Solna. The controls were women with benign lesions, e.g. myoma in the uterus or benign cystic adenoma. The cancer patients were had a mean age of 65±12 (sdev) year. The cancer patients were diagnosed at the Gyneacology Ultrasound department, Karolinska University Hospital, See Table 3 below.

TABLE 3

Control and cancer patients - Study 1B

| Patient Group | Diagnosis | N | Age (Average) | Age (SDEV) |
|---|---|---|---|---|
| HC | Healthy volunteers (see study 3) | 10 | 55 | 6 |
| BC | Benign lesions | 16 | 62 | 14 |
| LC | Early EOC - for prediction test of model | 8 | 67 | 15 |
| SC | Advanced EOC - for building a multivariate prediction model | 20 | 64 | 11 |
| SC | Advanced EOC - for prediction test of model | 11 | 68 | 13 |

The same method for sample isolation and preparation was used as in example 1A above.

Data Analysis

Partial Least Squares (PLS) was used to model the data (PLS-regression: a basic tool of chemometrics Chemometrics and Intelligent laboratory systems Wold S, Sjöström M, Eriksson, L, 2001, 58, 109-130). It is a regression method that reduces the dimensions in the data through maximising the covariance of the predictor matrix (X) with the response matrix (Y), keeping the corresponding dimensions (PLS components/latent variables). It is possible to identify variables that are important for the relationship between X and Y. One such variable importance measure is the Variable Importance in the Projection (VIP) parameter. VIP is a weighted sum of squares of the PLS weights, with the weights calculated from the amount of Y-variance of each PLS component in the model. Here, the predictor matrix is the 2DE data, and the response is a binary vector denoting class membership, in this case zeros represents the control (BC) class and ones represents the cancer (SC) class (Tab. 3). To determine the class memberships for new samples predicted with the model, a cutoff is set for the y, such that if the predicted y value is below the cutoff, the predicted class membership will be BC in this case, and if the predicted y value is above the cutoff, the predicted class membership will be SC. We selected a cutoff=0.5. The PLS modeling was carried out in SIMCA P v13.0 (Umetrics AB, Sweden).

Alternatively, variables (protein spots) were selected using statistical tools (ANOVA) provided by the image analysis software SameSpots (Nonlinear Dynamics).

Identification of Proteins by Mass Spectrometry Analysis

Silver-stained protein spots were excised from the gels, treated for in-gel digestion and analyzed at the Ludwig Institute, Uppsala, essentially as described previously (Hellman, U. (2000) Sample preparation by SDS/PAGE and in-gel digestion. EXS 88, 43-54.). Briefly, the silver was destained using Farmer's reagent, and trypsin (porcine, modified, sequence grade, Promega, Madison, Wis.) was introduced to the dried gel pieces. After overnight tryptic digestion, the peptides were bound to a C18 ZipTip column, washed, and then eluted with acetonitrile containing the matrix (alfa-cyano 4-hydroxy cinnamic acid) directly onto the target plate. The mass lists were generated by MALDI-TOF mass spectrometry on an Ultraflex III TOF/TOF from Bruker Daltonics, Bremen, Germany. The search for identity was performed using the search engine MASCOT (Matrix Science, London, England) by scanning the current version of NCBI nr sequence database. The spectrum was internally calibrated using autolytic tryptic peptides, and the tolerance was set at 0.02 Da. Oxidation of methionine was allowed. The significance of the identity was judged from the search engine's scoring system.

Results

Image analysis of 2D gels resulted in 1283 detected, matched, selected and analyzed protein spots (variables) representing the complete dataset (patient groups described in Tab. 3).

Figure 5:
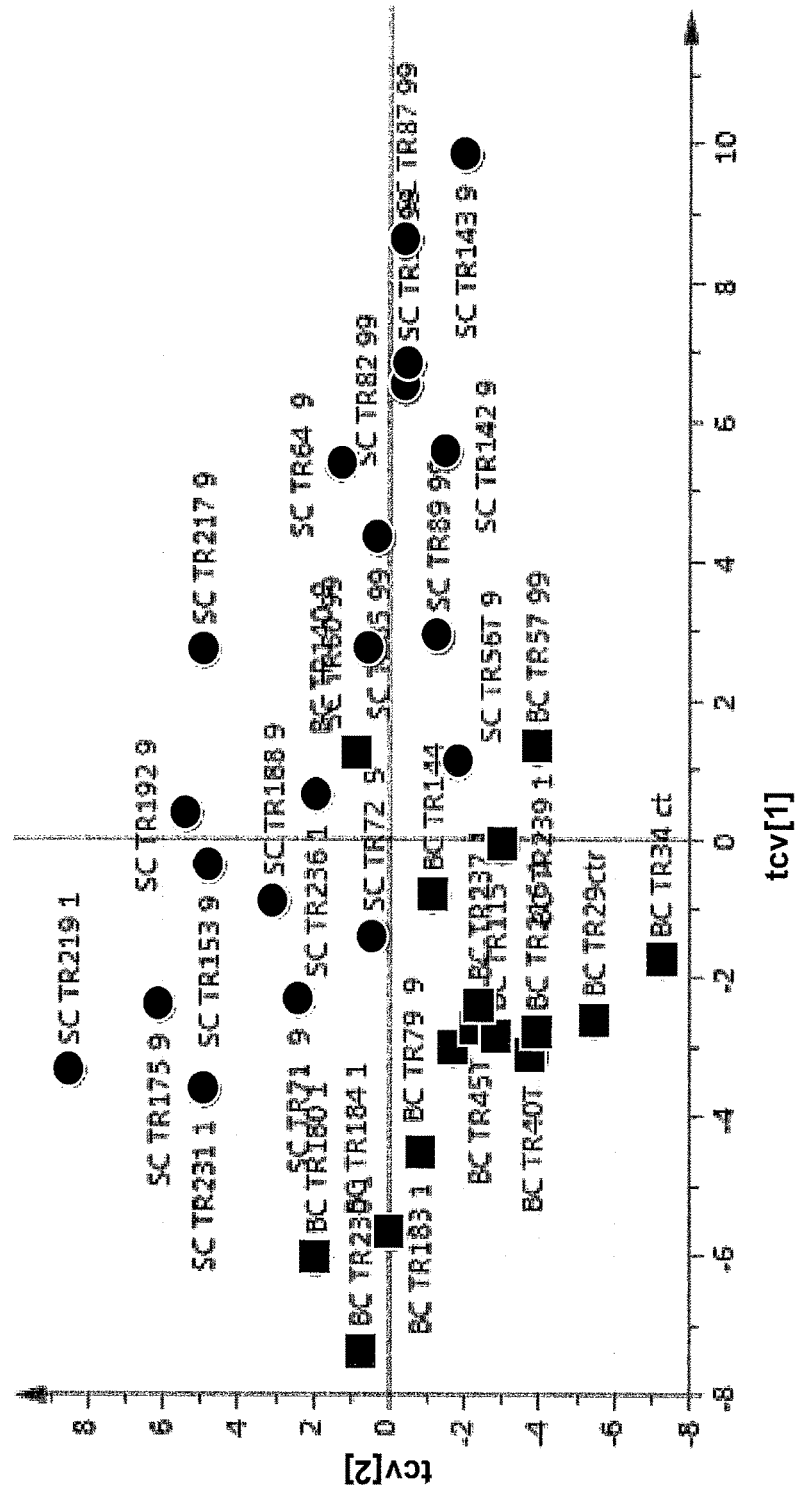
FIG. 5 shows Partial Least Square (PLS) model from study 1B of samples representing spread cancer versus controls. Black dots represent spread cancer samples and the black squares represent the controls.

After image analysis of 2D-gel separated proteins, data representing all samples were further analyzed by multivariate statistics (partial least square discriminant analysis, PLS). All data were normalized before analysis and prior to multivariate modelling, data were also pre-processed (log 2 transformed). A PLS model with two components showed the best results (FIG. 5). A sensitivity of 90% and a specificity of 94% was obtained for the optimized and cross validated model.

Variables were ranked according to their contribution to the prediction using the VIP parameter. Top-ranked variables (protein spots) were then selected for identification by mass spectrometry. Successful identifications are listed in table 4 below.

To evaluate the model, an independent test set of eleven SC and eight LC samples was used. A model was built on the training set with the model parameters selected from the model optimization procedure. We selected a cutoff=0.5. Nine of eleven SC samples and all eight LC samples were correctly classified, which correspond to a 89% sensitivity for the classification model.

Example 3—Study 1C

The main objective in study 1a and 1B was to describe a panel of biomarkers that can be used to diagnose a pelvic mass as malignant at an early stage. However, here in study 10 we describe an additional panel that indicate a deviation from the normal healthy condition. This deviation may then be of a benign nature or a cancer, and the panel described in study 1A and 1B will thereafter be necessary for the following cancer diagnosis.

All materials and methods were the same as described in study 1A and 1B. Patient samples corresponding to healthy

TABLE 4

Identification of biomarkers in Study 1B - based on PLS model

| Protein identity | Acc # EMBL (1) | Uniprot Acc # (2) | Spot no. (3) | Observed Mw (kDa)/pI | Theroetical Mw (kDa)/pI | VIP Rank (4) |
|---|---|---|---|---|---|---|
| Endoplasmic reticulum resident protein 29 (ERP29, ERP28, ERP31) | NP_006808 (¤) | P30040 (ERP29_HUMAN) | 1525* | 24/6.8 | 29/6.8 | 1 |
| ACTN4 protein | AAH15620 (¤) | Q96BG6 (Q96BG6_HUMAN) | 1836* | 72/5.5 | 74/5.2 | 3 |
| HP protein | AAH70299 | Q6NSB4 (Q6NSB4_HUMAN) | 1803* | 40/5.3 | 32/8.5 | 4 |
| Talin-1 | AAF27330 | Q9Y490 (TLN1_HUMAN) | 1821 | 50/6.9 | 272/5.8 | 6 |
| Proto-oncogene tyrosine-protein kinase Src | AAH11566 | P12931 (SRC_HUMAN) | 1821 | 50/6.9 | 60/6.1 | 6 |
| 3-mercaptopyruvate sulfurtransferase (Rhodanese) | CAA42060 | P25325 (THTM_HUMAN) | 1177 | 37/6.6 | 33/6.0 | 7 |
| HP protein | AAH70299 | Q6NSB4 (Q6NSB4_HUMAN) | 1155 | 40/5.5 | 32/8.5 | 8 |
| Talin-1 | AAF27330 | Q9Y490 (TLN1_HUMAN) | 758 | 60/6.0 | 272/5.8 | 10 |
| Talin-1 | AAF27330 | Q9Y490 (TLN1_HUMAN) | 755* | 58/5.8 | 272/5.8 | 11 |
| Talin-1 | AAF27330 | Q9Y490 (TLN1_HUMAN) | 292 | 100/6.0 | 272/5.8 | 12 |
| Integrin beta-3 (Platelet glycoprotein IIIa/CD61) | AAA52600 | P05106 (ITB3_HUMAN) | 792* | 56/ | 87/5.0 | 13 |
| Heat shock 70 kDa protein 1A/1B (HSX70) | AAA52697 | P08107 (HSP71_HUMAN) | 482 | 77/6.0 | 70/5.4 | 16 |
| Tubulin alpha-4A chain | NP_001265481 | P68366 (TBA4A_HUMAN) | 1801* | 55/5.2 | 49/4.9 | 19 |
| Integrin alpha-Iib (Platelet glycoprotein Iib) | CAA29987 | P08514 (ITA2B_HUMAN) | 911 | 67/5.5 | 71/5.2 | 24 |
| Tubulin, highly similar to Tubulin alpha-ubiquitous chain | BAG51785 | B3KPS3 (B3KPS3_HUMAN) | 1894 | 55/5.1 | 46/5.0 | 25 |
| crk-like protein CRKL | NP_005198 | P46109 (CRKL_HUMAN) | 1539* | 23/6.8 | 34/6.3 | 26 |
| Talin-1 | AAF27330 | Q9Y490 (TLN1_HUMAN) | 774 | 60/6.6 | 272/5.8 | 27 |
| Stress-70 protein, mitochondrial (MTHSP75) | AAA67526 | P38646 (GRP75_HUMAN) | 311 | 99/5.9 | 74/6.0 | 32 |
| Keratin, type II cytoskeletal 1 | NP_006112 | P04264 (K2C1_HUMAN) | 1870 | 55/5.5 | 66/8.2 | 33 |
| Gelsolin (Gesolin isoform a) | NP_000168 | P06396 (GELS_HUMAN) | 397 | 95/5.7 | 86/5.9 | 34 |
| Tubulin beta-1 chain | NP_110400 ($) (¤) | Q9H4B7 (TBB1_HUMAN) | 999 | 40/5.6 | 51/5.1 | 37 |
| Heat shock 70 kDa protein 8 isoform 2 variant | BAD96348 | Q53HF2 (Q53HF2_HUMAN) | 368 | 95/5.8 | 53/5.6 | 39 |
| Fibrinogen gamma chain, isoform CRA_o | EAX04921 | P02679 (FIBG_HUMAN) | 1854 | 47/5.7 | 48/5.5 | 40 |
| Integrin alpha2b, CD41 platelet glycoprotein IIb (of IIb/IIIa complex), | EAW51594 (¤) ($) | P08514 (ITA2B_HUMAN) | 276 | 95/5.0-5.5 | 104/5.4 | 45 |
| Talin-1 | AAF27330 | Q9Y490 (TLN1_HUMAN) | 1409 | 30/6.5 | 272/5.8 | 50 |
| Gelsolin (Gesolin isoform b) | NP_937895 | P06396 (GELS_HUMAN) | 401 | 90/5.9 | 81/5.6 | 79 |
| Ribonuclease inhibitor | 1A4Y | P13489 (RINI_HUMAN) | 1054* | 45/4.5 | 50/4.7 | — |

Figure 6:
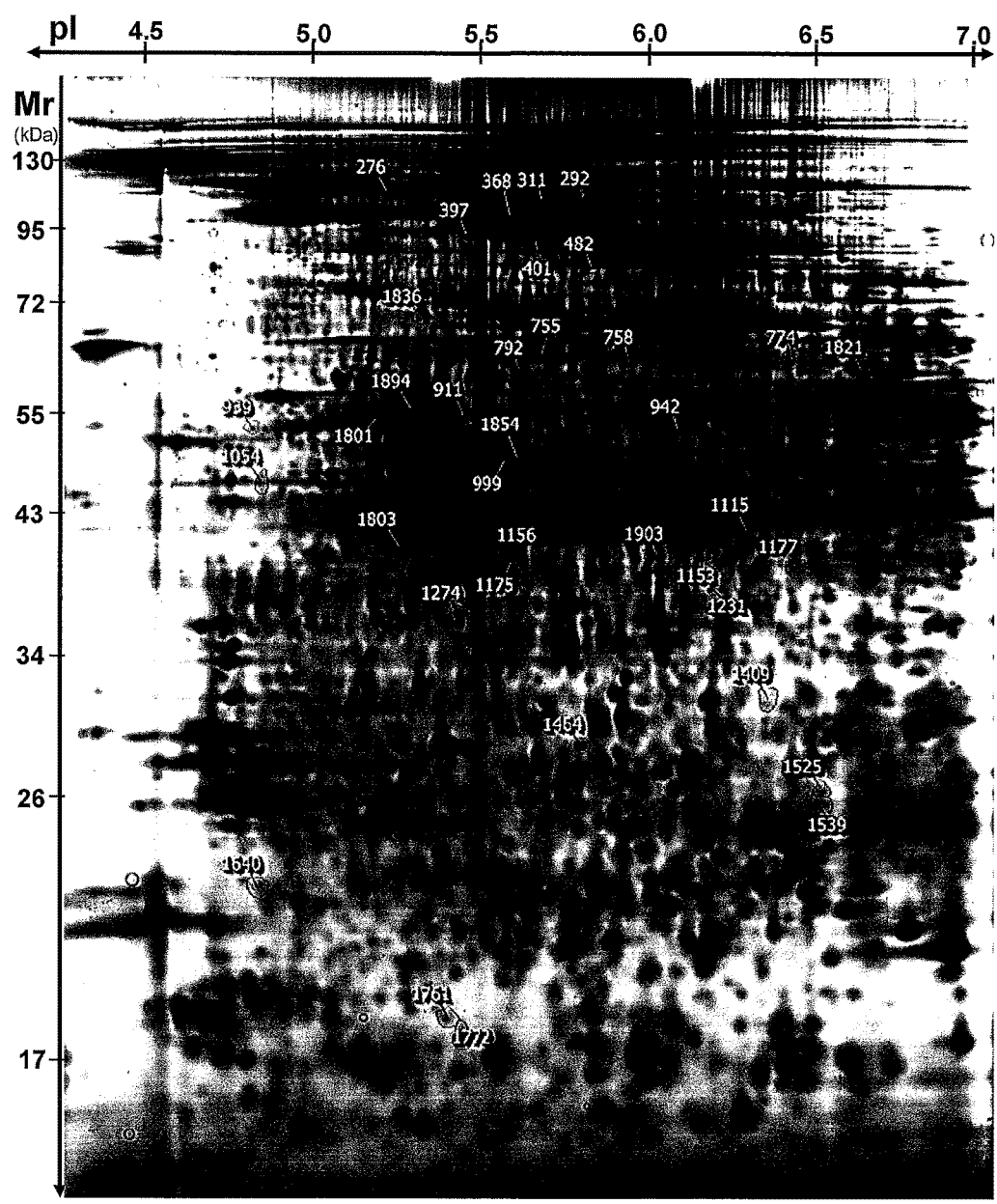
FIG. 6 shows the result from study 1B of a 2D gel separation of platelet proteins on a 2DE gel, where identified spots are marked out. Arrows and spot numbers indicate the location of identified biomarkers.
Figure 7:
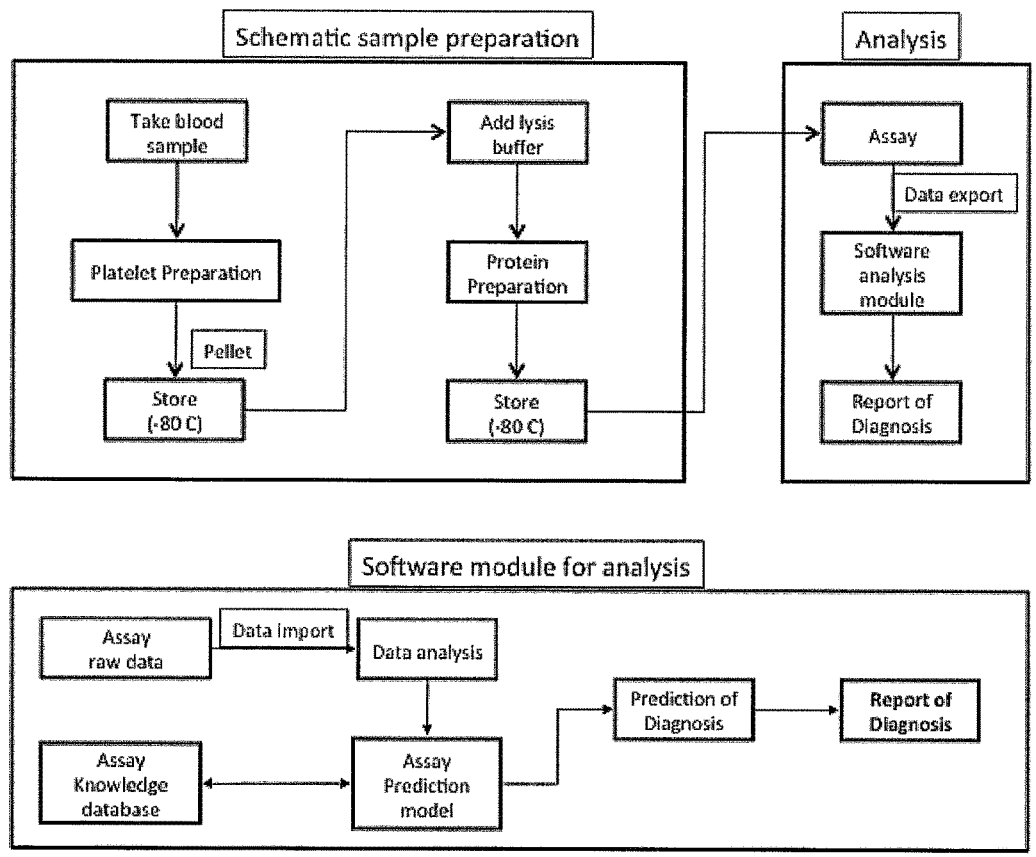
FIG. 7 shows a schematic example of an embodiment of the invention. Sample preparation: A blood sample is taken and from that platelets are separated out using sequential centrifugation steps. The final pellet is then stored at −80° C. or processed directly. To the pellet is then lysis buffer added and non-lysed cells are removed by centrifugation. The sample is then stored at −80° C. or taken directly to the assay. The assay is antibody based (i e an ELISA or similar) and run on existing instrumentation for that type of assay. The read-out from the instrument is then analysed in the standard computer/software. For the specific analysis of the biomarker panel a dedicated algorithm is incorporated in the instrument software.

(1) - primary EMBL accession number based on mass spectrometry data
(2) - corresponding UNIPROT accession number
(3) - spot number # given by the SameSpot software, see FIG. 6 for position on 2D reference map
*these biomarker candidates were also altered significant according to ANOVA test (P < 0.05)
($) - these biomarker candidates were also described in study 1 (example 1)
(¤) - these biomarker candidates were also found in study 1

The complete data set analysed by ANOVA (selection criteria: p<0.05, q<0.05, fold change >1.5×) produced complementary results.

controls (HC) are described in table 3. Ten markers showed significantly (P<0.01) different levels between samples from HC and BC and/or cancer (SC/LC): KAP3, CNDP2, ILEU, SPB6, SHLB1, CAZA1, PHB, TMP1, GPIX and AP4A. All markers are described in Tab 5 below.

This panel of biomarker candidates show significant (p<0.01) difference in expression between healthy subjects and subjects suffering from benign and/or malignant pelvic mass of possible ovarian origin.

analysis show separation between healthy controls and advanced cancers. Protein biomarker candidates identified in this study indicate a significant overlap with markers identified from ovarian cancer. However, a number of not yet identified biomarker candidates show differential expression between prostate and ovarian cancer.

TABLE 5

Biomarkers from study 1C discriminating lesions from healthy subjects

| Protein identity | Acc # EMBL | Uniprot Acc # | Spot no. | Observed Mw (kDa)/pI | Theroetical Mw (kDa)/pI |
|---|---|---|---|---|---|
| KAP3, cAMP-dependent protein kinase subunit RII-beta | AAA60099 | P31323 (KAP3_HUMAN) | 939 | 54/4.9 | 47/4.8 |
| CNDP2, Cytosolic non-specific dipeptidase | BAG53426 | Q96KP4 (CNDP2_HUMAN) | 942 | 50/6.2 | 53/5.6 |
| ILEU, Leukocyte elastase inhibitor | NP_109591 | P30740 (ILEU_HUMAN) | 1115 | 43/6.5 | 43/5.9 |
| ILEU, Leukocyte elastase inhibitor | NP_109591 | P30740 (ILEU_HUMAN) | 1153 | 40/6.2 | 43/5.9 |
| SPB6, serpin B6 | NP_001258751 | P35237 (SPB6_HUMAN) | 1175 | 40/5.7 | 44/5.3 |
| SHLB1, Endophilin-B1 isof.1 | NP_057093 | Q9Y371 (SHLB1_HUMAN) | 1231 | 38/6.2 | 41/5.8 |
| CAZA1, F-actin-capping protein subunit alpha-1 | NP_006126 | P52907 (CAZA1_HUMAN) | 1274 | 38/5.6 | 33/5.5 |
| PHB, Prohibitin | AAS88903 | Q6PUJ7 (Q6PUJ7_HUMAN) | 1464 | 28/6.0 | 30/5.6 |
| TMP1, tropomyosin alpha-1 | XP_005254707 | F5H7S3 (F5H7S3_HUMAN) | 1640 | 20/5.0 | 29/4.8 |
| GPIX, Glycoprotein IX (CD42a) | AAH30229 | P14770 (GPIX_HUMAN) | 1761 | 18/5.4 | 19.6/5.9 |
| AP4A, Bis(5'-nucleosyl)-tetraphosphatase | NP_001152 | P50583 (AP4A_HUMAN) | 1772 | 17/5.1 | 17/5.2 |

Example 4—Study 2

Diagnosis of prostate cancer is very demanding for the patients today. The commonly used biomarker PSA is only an indicative measurement. This leads to the fact that an increased level of PSA results in the need for biopsies. This is very cumbersome and the side effects are significant. Initially, up to 5% of the patients have to go to the emergency within a day to get treatment for sepsis. There are then also problems with loss of sexual functionality. The worst side effect is the potential risk of spreading viable cancer cells as a consequence of the biopsy procedure. Based on these facts there is an urgent need of improved and more reliable tools for diagnosis of prostate cancer.

We collected blood samples using same protocols as for the ovarian cancer project (study 1). In total, samples from 49 male patients were collected from the Urologic clinic at Karolinska University Hospital. All patients showed high PSA (prostate specific antigen) score and the diagnosis was graded according to the TNM classification, T1-T3. The oldest patient was born in 1936 and was 76 of age at the date of the cancer diagnosis. The youngest was born in 1960 and he was 53 years old at the time of diagnosis.

Samples from healthy controls were collected (10 males volunteers). All subjects were included in the "Stockholm 2 study" (at Danderyd Hospital) where patients give biopsy material for the prostate biobanking and screening project. All controls showed low PSA levels and were declared healthy. The oldest in this group was born 1942 and the youngest was born in 1957; 70 years old resp. 56 years old at the time of blood collection.

For study 2 we included 10 healthy controls, 10 patients at stage T3 (corresponding advanced cancer), 9 patients at stage T2 and 2 patients at stage 1. The T1 and T2 groups were regarded as early cancer. All samples were prepared and analyzed as previously described (study 1).

Preliminary data show that the biomarker profile is very similar to results from study 1 (ovarian cancer). PCA The biomarkers identified in study 1 and study 2 for ovarian and prostate cancer is summarized in table 6 below.

TABLE 6

Biomarker candidates described in studies 1-2, ovarian cancer and prostate cancer

| Protein identity, (Acc # EMBL or Uniprot Acc #) | Study |
|---|---|
| ACTN1, ACTN1 protein, (A1L0V1_HUMAN) | 1a, 2, 3, 4 |
| ACTN4, (Q96BG6_HUMAN) | 1a, 1b, 2 |
| CRKL, crk-like protein (CRKL_HUMAN) | 1b, 2 |
| ERP29, Endoplasmic reticulum resident protein 29 (ERP29_HUMAN) | 1a, 1b, 2 |
| FERM, Fermitin family homolog 3, (URP2_HUMAN) | 1a, 2 |
| FIBG, Fibrinogen gamma chain, isoform CRA_o (FIBG_HUMAN) | 1b, 2 |
| FLNA, FLNA protein, Q96C61_HUMAN | 1a, 2 |
| GELS, Gelsolin (GELS_HUMAN) | 1b, 2, 3, 4 |
| GRP75, Stress-70 protein, mitochondrial (GRP75_HUMAN) | 1b, 2 |
| HP protein (Q6NSB4_HUMAN) | 1b, 2 |
| HSP70, Heat shock 70 kDa protein 8 isoform 2 variant (Q53HF2_HUMAN) | 1b, 2 |
| HSP71, Heat shock 70 kDa protein 1A/1B (HSX70) (HSP71_HUMAN) | 1b, 2 |
| ITA2B (ITGA2B), Integrin alpha2b, CD41 (ITA2B_HUMAN) | 1a, 2, 3, 4 |
| ITB3, Integrin beta-3 (ITB3_HUMAN) | 1b, 2, 3, 4 |
| RINI, Ribonuclease inhibitor (RINI_HUMAN) | 1b, 2, 3, 4 |
| SRC, Proto-oncogene tyrosine-protein kinase Src (SRC_HUMAN) | 1b, 2 |
| TBA, Tubulin, highly similar to Tubulin a (B3KPS3_HUMAN) | 1b, 2 |
| TBA4A, Tubulin alpha-4A chain (TBA4A_HUMAN) | 1b, 2, 3, 4 |
| THTM, 3-mercaptopyruvate sulfurtransferase (THTM_HUMAN) | 1b, 2 |
| TLN1, Talin-1 (TLN1_HUMAN) | 1b, 2, 3, 4 |
| TUBB1, Tubulin beta-1 chain (TBB1_HUMAN) | 1a, 1b, 2, 3, 4 |
| VCL, Vinculin (VINC_HUMAN) | 1a, 2, 3, 4 |
| WDR1, WD repeat-containing protein 1 isoform 1 (Q59ER5_HUMAN) | 1a, 2, 3, 4 |

Example 5—Study 3 and 4

Pancreatic and colorectal cancer are some of the most lethal malignancies worldwide and thus demonstrates an urgent demand for improved screening tools for early detection. Yet, despite the implementation of current screening programs about 50% of these malignancies are detected at advanced tumor stages.

Though remarkable advances have been achieved based on clinical and preclinical research, these have not translated to equal noteworthy improvements at the bedside. In present clinical practice, screening for pancreatic and colorectal cancer is based on state-of-the art imaging or even invasive diagnostics. Diagnostic modalities comprise endoscopic ultrasound (EUS), explorative laparoscopy/laparotomy, computed tomography (CT), and magnetic resonance imaging (MRI).

Based on the possibility that that the proteome of platelets from healthy donors could be different to those from patients with carcinomas of the colon and pancreas, the aim of the present study was to analyze using two-dimensional gel-electrophoresis (2-DE) whether the platelets may be different in terms of protein expression in the distinct groups. In total, we screened 12 samples from patients with pancreatic cancer, 12 samples from patients with colorectal cancer and 12 healthy subjects by means of 2-DE and mass spectrometry to identify the cancer-associated protein repertoire and the corresponding tumor-associated proteins of platelets.

Materials and Methods

Patients

The study was approved by the local Ethics Committee. All patients included in the study signed a written informed consent. Patients were divided into healthy controls (n=12) and patients with pancreatic (n=12) and colorectal (n=12) carcinomas. Blood samples were obtained by and collected in sample-tubes for platelet isolation.

Platelet Isolation

Human blood was collected into 9 ml monovettes containing EDTA and centrifuged in a standard laboratory centrifuge at 200×g for 20 min at room temperature. Subsequently, the plasma without buffy coat was carefully transferred into a new 2.0 ml reaction tube and diluted with 1,300 µl PBS buffer. After a second centrifugation step at 800×g for 10 min at room temperature, the supernatant was removed and the platelets were resuspended in lysis buffer for storage at −80° C.

Two-Dimensional Gel Electrophoresis (2-DE)

Protein quantification was carried out using the EZQ Protein Quantitation Kit (Invitrogen). After labeling the proteins of each sample and the internal standard with fluorescence dyes (NH DyeAGNOSTIC), 150 µg protein per gel (2×50 µg sample plus 50 µg internal standard) were dissolved in 450 µL rehydration sample buffer [7 M urea, 2 M thiourea, 2% CHAPS, 2% ampholytes (pH 4-7, Serva), 0.3% DTT, and a trace of bromphenolblue]. First dimension was accomplished on immobilized pH gradient (IPG) strips 4-7, 24 cm (GE Healthcare), and second dimension by SDS-polyacrylamid gel electrophoresis (PAGE) on 12.5% precast gels (Serva). Gel images were scanned immediately by using Typhoon FLA 9000 (GE Healthcare) following the SDS-PAGE. The fold change of the protein expression levels between groups was obtained from in-gel analysis by using the software Progenesis SameSpots (v4.1, Nonlinear Dynamics).

Matrix-Assisted Laser Desorption/Ionization Mass Spectrometry (MALDI-MS)

For matrix-assisted laser desorption/ionization time of flight (MALDI-TOF) mass spectrometry analysis significant spots were automatically cut and washed multiple times to remove staining dye and other inhibitory chemicals. Dried gel spots were rehydrated in an ice cold solution of 12.5 ng/µL sequencing grade trypsin (Promega) in 10 mM $NH_4HCO_3$. Proteins were digested in-gel at 37° C. for 4 h. Peptides were extracted for 30 min with 10 µL of 0.1% TFA and directly applied to a MALDI Pre-spotted AnchorChip target (Bruker Daltoniks) according to the manufacturer's instructions.

Subsequently, samples were analyzed in a time-of-flight Ultraflex-Tof/Tof mass spectrometer (Bruker Daltoniks). Acquired mass spectra were automatically calibrated, annotated using Compass 1.3 software (Bruker Daltoniks) and results from each individual spot were used to search a human sub-set of Swiss-Prot (Sprot_57.8, 20401 protein entries) non-redundant database using Mascot search engine (Version 2.2, Matrix Science Ltd) in consideration of the following settings: enzyme "trypsin", species "human", fixed modifications "carbamidomethyl", optional modifications "Methionine oxidation" and missed cleavages "1". Mass tolerance was set to 50 ppm. Using these settings, a mascot score of greater than 70 was taken as significant ($p<0.01$).

Results

Protein expression was compared between the platelets of tumor (pancreas & colon) and normal samples using a 2-DE multiplex-fluorescence technology (NH DyeAGNOSTIC) with a mixed internal standard containing protein extracts of all 36 patients included in the study. After 2-DE, the analysis of the Cyt, Cy3, and Cy5 gel images with the SameSpots software revealed changes in the abundance of 35 proteins with a statistical significance between the pancreas tumor and normal spot volume ratios and 36 protein with a statistical significance between the colon tumor and normal spot volume ratios ($p<0.05$). All proteins were excised from the gels and further analyzed by mass spectrometry.

In summary, these studies revealed a new individual pattern of unique proteins with the potential to diagnose carcinoma with higher specificity and sensitivity than previously reported serum biomarkers, see FIGS. 8-10, and tables 7-8.

TABLE 7

Biomarker candidates described in study 3, colorectal cancer

| Protein identity, (Acc # EMBL or Uniprot Acc #) | Study |
|---|---|
| ACTB, P60709 (ACTB_HUMAN) | 3, 4 |
| ACTN1, ACTN1 protein, (A1L0V1_HUMAN) | 1a, 2, 3, 4 |
| CASP3, P42574 (CASP3_HUMAN) | 3, 4 |
| CFL1, P23528 (COF1_HUMAN), Cofilin | 3, 4 |
| CLU, P10909 (CLUS_HUMAN), Clustrin | 3, 4 |
| FPPS_Human | 3, 4 |
| GELS, Gelsolin (GELS_HUMAN) | 1b, 2, 3, 4 |
| GSTO1, P78417 (GSTO1_HUMAN), Glutathione S-transferase omega-1 | 3 |
| HDHD2_Human, Q9H0R4 (HDHD2_HUMAN) | 3, 4 |
| ITA2B (ITGA2B), Integrin alpha2b, CD41 (ITA2B_HUMAN) | 1a, 2, 3, 4 |
| ITB3, Integrin beta-3 (ITB3_HUMAN) | 1b, 2, 3, 4 |
| ITGA6, P23229 (ITA6_HUMAN) | 3, 4 |
| MLEC, (MLEC_Human) | 3, 4 |
| PHB, (Q6PUJ7_HUMAN) | 1c, 2, 3, 4 |
| RINI, Ribonuclease inhibitor (RINI_HUMAN) | 1b, 2, 3, 4 |
| SNCA, P37840 (SYUA_HUMAN), Alpha-synuclein | 3, 4 |
| SPB6, (SPB6_HUMAN), Serpin B6 | 1c, 2, 3, 4 |
| TBA4A, Tubulin alpha-4A chain (TBA4A_HUMAN) | 1b, 2, 3, 4 |

TABLE 7-continued

Biomarker candidates described in study 3, colorectal cancer

| Protein identity, (Acc # EMBL or Uniprot Acc #) | Study |
|---|---|
| TLN1, Talin-1 (TLN1_HUMAN) | 1b, 2, 3, 4 |
| TSG, Q99816 (TS101_HUMAN) | 3, 4 |
| TUBB1, Tubulin beta-1 chain (TBB1_HUMAN) | 1a, 1b, 2, 3, 4 |
| VCL, Vinculin (VINC_HUMAN) | 1a, 2, 3, 4 |
| WDR1, WD repeat-containing protein 1 isoform 1 (Q59ER5_HUMAN) | 1a, 2, 3, 4 |

TABLE 8

Biomarker candidates described in study 4, pancreatic cancer

| Protein identity, (Acc # EMBL or Uniprot Acc #) | Study |
|---|---|
| ACTB, P60709 (ACTB_HUMAN) | 3, 4 |
| ACTN1, ACTN1 protein, (A1L0V1_HUMAN) | 1a, 2, 3, 4 |
| CASP3, P42574 (CASP3_HUMAN) | 3, 4 |
| CFL1, P23528 (COF1_HUMAN), Cofilin | 3, 4 |
| CLU, P10909 (CLUS_HUMAN), Clustrin | 3, 4 |
| FPPS_Human | 3, 4 |
| GELS, Gelsolin (GELS_HUMAN) | 1b, 2, 3, 4 |
| HDHD2_Human, Q9H0R4 (HDHD2_HUMAN) | 3, 4 |
| HSP90AB1, Q6PK50 (Q6PK50_HUMAN) | 4 |
| ITA2B (ITGA2B), Integrin alpha2b, CD41 (ITA2B_HUMAN) | 1a, 2, 3, 4 |
| ITB3, Integrin beta-3 (ITB3_HUMAN) | 1b, 2, 3, 4 |
| ITGA6, P23229 (ITA6_HUMAN) | 3, 4 |
| MLEC, (MLEC_Human) | 3, 4 |
| PHB, (Q6PUJ7_HUMAN) | 1c, 2, 3, 4 |
| RINI, Ribonuclease inhibitor (RINI_HUMAN) | 1b, 2, 3, 4 |
| SNCA, P37840 (SYUA_HUMAN), Alpha-synuclein | 3, 4 |
| SPB6, (SPB6_HUMAN), Serpin B6 | 1c, 2, 3, 4 |
| TBA4A, Tubulin alpha-4A chain (TBA4A_HUMAN) | 1b, 2, 3, 4 |
| TLN1, Talin-1 (TLN1_HUMAN) | 1b, 2, 3, 4 |
| TSG, Q99816 (TS101_HUMAN) | 3, 4 |
| TUBB1, Tubulin beta-1 chain (TBB1_HUMAN) | 1a, 1b, 2, 3, 4 |
| VCL, Vinculin (VINC_HUMAN) | 1a, 2, 3, 4 |
| WDR1, WD repeat-containing protein 1 isoform 1 (Q59ER5_HUMAN) | 1a, 2, 3, 4 |

Example 6

Early detection of ovarian cancer is very difficult, but crucial for early initiation of therapy and survival.

A blood sample is obtained from the patient by clinical standard procedures and the platelet fraction is prepared according to methods described in Example 1. A platelet lysate is prepared and proteins are separated, biomarkers (specified in Table 2 and FIG. 2) are detected and quantified according to methods described in Example 1.

The relative quantity of markers is calculated according to the diagnostic algorithm (3). The output value from the diagnostic algorithm is then compared to the defined cut off value, preferably 0.29. An output value above 0.29 then indicates high risk for ovarian cancer and further examination and subsequent therapy should therefore be initiated as soon as possible.

Example 7

The results obtained for a patient according to Example 1-2, or 4-5 is used to select appropriate treatment regimen for improved prognosis of the patient. For patients identified with cancer, treatment is initiated without delay, according to recommended care program.

Example 8

Platelet Based Diagnosis of Ovarian Cancer Using Quantitative Antibody Based Technology In a practical clinical setting when we need to perform diagnosis using a method that measures the above-mentioned biomarkers, and using an antibody based technology, the following scenario is applicable:

(1) Using preparations of platelets from at least 20 benign controls and 20 patients with advanced ovarian cancer, mentioned biomarker panel is analyzed by quantitative Western blot (alternatively ELISA or Luminex based technology). Quantitative signals for each biomarker is then normalized to a quantitative signals of an appropriate chosen internal standard (e.g. GAPDH or gamma 14-3-3, Baumgartner R, et al. Identification and validation of platelet low biological variation proteins, superior to GAPDH, actin and tubulin, as tools in clinical proteomics. J. Proteomics, 2013 (94) 540-51).

(2) Data is then analyzed by appropriate multivariate software (e.g. SIMCA P v13, Umetrics AB) as described in Example 2. This procedure results in a prediction model to be used as a prediction tool for diagnosis of new unknown samples. The prediction model provides for each new sample a value between 0 and 1, where values >0.5 indicate cancer and values <0.5 indicate benign lesions. This procedure can be used to build a local prediction database using standardized procedures and in addition, results may be compared with the corresponding databases from other certified analysis laboratories.

(3) After a final diagnosis, obtained on the basis of histopathological examination of surgical tissue sample corresponding the previously unknown sample, information (diagnosis and biomarker levels) can be added to the local prediction database (see 1 above). Through this interactive process, the prediction model is gradually being upgraded in order to achieve increased sensitivity and specificity.

In summary, the individual studies together detected 45 unique protein markers, for use in early non-invasive cancer diagnostics, as described in the present invention. All these markers, and in which study they were identified is described in Table 9 below.

TABLE 9

Summary table, Biomarker candidates (n = 45) described in any of the studies 1-4

| Protein identity (Acc # EMBL or Uniprot Acc #) | Study |
|---|---|
| ACTB, P60709 (ACTB_HUMAN), Actin, cytoplasmic 1 | 3, 4 |
| ACTN1, A1L0V1 (A1L0V1_HUMAN), ACTN1 protein, Alpha-actinin-1 related | 1a, 2, 3, 4 |
| ACTN4, Q96BG6 (Q96BG6_HUMAN), Alpha-actinin-4 related | 1a, 1b, 2 |
| AP4A, P50583 (AP4A_HUMAN), Bis(5'-nucleosyl)-tetraphosphatase | 1c |
| CASP3, P42574 (CASP3_HUMAN), Caspase-3 | 3, 4 |
| CAZA1, P52907 (CAZA1_HUMAN), F-actin-capping protein subunit alpha-1 | 1c, 2 |
| CFL1, P23528 (COF1_HUMAN), Cofilin | 3, 4 |

TABLE 9-continued

Summary table, Biomarker candidates (n = 45) described in any of the studies 1-4

| Protein identity (Acc # EMBL or Uniprot Acc #) | Study |
|---|---|
| CLU, P10909 (CLUS_HUMAN), Clustrin | 3, 4 |
| CNDP2, Q96KP4 (CNDP2_HUMAN), Cytosolic non-specific dipeptidase | 1c, 2 |
| CRKL, P46109 (CRKL_HUMAN), Crk-like protein | 1b, 2 |
| ERP29, P30040 (ERP29_HUMAN), Endoplasmic reticulum resident protein 29 | 1a, 1b, 2 |
| FERM, Q86UX7 (URP2_HUMAN), Fermitin family homolog 3 | 1a, 2 |
| FIBG, P02679 (FIBG_HUMAN), Fibrinogen gamma chain, isoform CRA_o | 1b, 2 |
| FLNA, Q96C61 (Q96C61_HUMAN), FLNA protein | 1a, 2 |
| FPPS, P14324 (FPPS_HUMAN), Farnesyl pyrophosphate synthase | 3, 4 |
| GELS, P06396 (GELS_HUMAN), Gelsolin | 1b, 2, 3, 4 |
| GPIX, P14770 (GPIX_HUMAN) (CD42a), Platelet glycoprotein IX | 1c, 2 |
| GRP75, P38646 (GRP75_HUMAN), Stress-70 protein, mitochondrial | 1b, 2 |
| GSTO1, P78417 (GSTO1_HUMAN), Glutathione S-transferase omega-1 | 3 |
| HDHD2, Q9H0R4 (HDHD2_HUMAN), Haloacid dehalogenase-like hydrolase domain-containing protein 2 | 3, 4 |
| HP protein, Q6NSB4 (Q6NSB4_HUMAN), HP protein | 1b, 2 |
| HSP70, Q53HF2 (Q53HF2_HUMAN), Heat shock 70 kDa protein 8 isoform 2 variant | 1b, 2 |
| HSP71, P08107 (HSP71_HUMAN), Heat shock 70 kDa protein 1A/1B (HSX70) | 1b, 2 |
| HSP90AB1, Q6PK50 (Q6PK50_HUMAN), HSP90AB1 protein | 4 |
| ILEU, P30740 (ILEU_HUMAN), Leukocyte elastase inhibitor | 1c, 2 |
| ITA2B or ITGA2B, P08514 (ITA2B_HUMAN), Integrin alpha 2b, CD41 | 1a, 2, 3, 4 |
| ITB3, P05106 (ITB3_HUMAN), Integrin beta-3, CD61 | 1b, 2, 3, 4 |
| ITGA6, P23229 (ITA6_HUMAN), Integrin alpha-6, CD49f | 3, 4 |
| KAP3, P31323 (KAP3_HUMAN), cAMP-dependent protein kinase type II-beta regulatory subunit | 1c, 2 |
| MLEC, Q14165 (MLEC_Human), Malectin | 3, 4 |
| PHB, Q6PUJ7 (Q6PUJ7_HUMAN), Prohibitin | 1c, 2, 3, 4 |
| RINI, P13489 (RINI_HUMAN), Ribonuclease inhibitor | 1b, 2, 3, 4 |
| SHLB1, Q9Y371 (SHLB1_HUMAN), Endophilin-B1 isof.1 | 1c |
| SNCA, P37840 (SYUA_HUMAN), Alpha-synuclein | 3, 4 |
| SPB6, P35237 (SPB6_HUMAN), Serpin B6 | 1c, 2, 3, 4 |
| SRC, P12931 (SRC_HUMAN), Proto-oncogene tyrosine-protein kinase Src | 1b, 2 |
| TBA, B3KPS3 (B3KPS3_HUMAN), Tubulin, highly similar to Tubulin alpha-ubiquitous chain | 1b, 2 |
| TBA4A, P68366 (TBA4A_HUMAN), Tubulin alpha-4A chain | 1b, 2, 3, 4 |
| THTM, P25325 (THTM_HUMAN), 3-mercaptopyruvate sulfurtransferase | 1b, 2 |
| TLN1, Q9Y490 (TLN1_HUMAN), Talin-1 | 1b, 2, 3, 4 |
| TMP1, F5H7S3 (F5H7S3_HUMAN), Tropomyosin alpha-1 chain | 1c, 2 |
| TSG, Q99816 (TS101_HUMAN), Tumor susceptibility gene 101 protein | 3, 4 |
| TUBB1, Q9H4B7 (TBB1_HUMAN), Tubulin beta-1 chain | 1a, 1b, 2, 3, 4 |
| VCL, P18206 (VINC_HUMAN), Vinculin | 1a, 2, 3, 4 |
| WDR1, Q59ER5 (Q59ER5_HUMAN), WD repeat-containing protein 1 isoform 1 | 1a, 2, 3, 4 |

The Studies revealed a panel of 12 biomarkers, which are applicable in the diagnosis of all four kinds of cancer described, see Table 10.

TABLE 10

Biomarker candidates common to all studies 1-4.

| Protein identity, (Acc # EMBL or Uniprot Acc #) | Study |
|---|---|
| ACTN1, ACTN1 protein, (A1L0V1_HUMAN) | 1a, 2, 3, 4 |
| GELS, Gelsolin (GELS_HUMAN) | 1b, 2, 3, 4 |
| ITA2B (ITGA2B), Integrin alpha2b, CD41 (ITA2B_HUMAN) | 1a, 2, 3, 4 |
| ITB3, Integrin beta-3 (ITB3_HUMAN) | 1b, 2, 3, 4 |
| PHB, (Q6PUJ7_HUMAN) | 1c, 2, 3, 4 |
| RINI, Ribonuclease inhibitor (RINI_HUMAN) | 1b, 2, 3, 4 |
| SPB6, (SPB6_HUMAN), Serpin B6 | 1c, 2, 3, 4 |
| TBA4A, Tubulin alpha-4A chain (TBA4A_HUMAN) | 1b, 2, 3, 4 |
| TLN1, Talin-1 (TLN1_HUMAN) | 1b, 2, 3, 4 |
| TUBB1, Tubulin beta-1 chain (TBB1_HUMAN) | 1a, 1b, 2, 3, 4 |
| VCL, Vinculin (VINC_HUMAN) | 1a, 2, 3, 4 |
| WDR1, WD repeat-containing protein 1 isoform 1 (Q59ER5_HUMAN) | 1a, 2, 3, 4 |

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of measuring platelet-derived biomarkers in a blood sample of a subject suspected of having an ovarian or prostate cancer lesion, said method comprising:
providing platelet-proteins extracted from platelets by lysis, wherein the platelets are isolated from a blood sample of the subject suspected of having an ovarian or prostate cancer lesion; and
measuring respective amounts of platelet-derived biomarkers endoplasmic reticulum protein 29 (ERP29) and α-actinin 4 (ACTN4) in the extracted platelet-proteins, wherein measuring respective amounts of platelet-derived biomarkers ERP29 and ACTN4 in the extracted platelet-proteins comprises contacting the extracted platelet-proteins with a first antibody that specifically binds ERP29 and with a second antibody that specifically binds ACTN4 and determining amounts of the first antibody specifically bound to ERP29 and the second antibody specifically bound to ACTN4, respectively.

2. The method according to claim 1, wherein the method further comprises measuring a respective amount of at least one additional platelet-derived biomarker selected from a group consisting of HP-protein, TLN1, SRC and THTM in the extracted platelet-proteins.

3. The method according to claim 1, wherein providing platelet-proteins extracted from platelets isolated from a blood sample of the subject suspected of having an ovarian or prostate cancer lesion comprises
   isolating platelets from a blood sample of said subject; and
   extracting platelet-proteins from said isolated platelets by lysis.

4. The method according to claim 1, wherein the method further comprises measuring respective amounts of at least two additional platelet-derived biomarkers selected from the group consisting of ACTN1, CRKL, FERM, FIBG, FLNA, GELS, GRP75, HP protein, HSP70, HSP71, ITGA2B, ITB3, RINI, SRC, TBA, TBA4A, THTM, TLN1, TUBB1, VCL and WDR1, in the extracted platelet-proteins.

5. A method of measuring platelet-derived biomarkers in a blood sample of a subject suspected of having an ovarian or prostate cancer lesion, comprising
   isolating platelets from a blood sample of said subject;
   extracting platelet-proteins from said isolated platelets by lysis;
   separating said extracted platelet-proteins on a two-dimensional gel electrophoresis gel;
   identifying respective platelet-derived biomarkers endoplasmic reticulum protein 29 (ERP29) and α-actinin 4 (ACTN4) on said two-dimensional gel electrophoresis gel; and
   measuring a respective amount of each of said identified platelet-derived biomarkers on said two-dimensional gel electrophoresis gel.

* * * * *

UNITED STATES PATENT AND TRADEMARK OFFICE
CERTIFICATE OF CORRECTION

PATENT NO. : 10,054,596 B2
APPLICATION NO. : 14/762394
DATED : August 21, 2018
INVENTOR(S) : Bo Franzèn et al.

Page 1 of 1

It is certified that error appears in the above-identified patent and that said Letters Patent is hereby corrected as shown below:

On the Title Page

Item "(60) Related U.S. Application Data", change "61/755,294" to --61/755,264--.

Item "(30) Foreign Application Priority Data", change "1350063" to --1350063-2--.

Signed and Sealed this
Thirteenth Day of November, 2018

Andrei Iancu
*Director of the United States Patent and Trademark Office*